(12) United States Patent
Lefeber et al.

(10) Patent No.: US 12,226,906 B2
(45) Date of Patent: Feb. 18, 2025

(54) DECENTRALIZED ROTARY ACTUATOR

(71) Applicant: VRIJE UNIVERSITEIT BRUSSEL, Brussels (BE)

(72) Inventors: Dirk Lefeber, Puurs (BE); David Rodríguez Cianca, Madrid (ES); Carlos David Rodriguez Guerrero, Ixelles (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 1164 days.

(21) Appl. No.: 17/047,164

(22) PCT Filed: Apr. 17, 2019

(86) PCT No.: PCT/EP2019/059900
§ 371 (c)(1),
(2) Date: Oct. 13, 2020

(87) PCT Pub. No.: WO2019/201982
PCT Pub. Date: Oct. 24, 2019

(65) Prior Publication Data
US 2021/0122040 A1    Apr. 29, 2021

(30) Foreign Application Priority Data

Apr. 17, 2018   (EP) .................................... 18167799

(51) Int. Cl.
*A61H 3/00*       (2006.01)
*B25J 9/00*       (2006.01)
(Continued)

(52) U.S. Cl.
CPC .............. *B25J 9/1633* (2013.01); *A61H 3/00* (2013.01); *B25J 9/0006* (2013.01); *B25J 13/085* (2013.01);
(Continued)

(58) Field of Classification Search
CPC ................ A61H 3/00; A61H 2201/149; A61H 2201/165; A61H 2201/5061; B25J 9/0006; B25J 9/1633; B25J 13/085
See application file for complete search history.

(56) References Cited

U.S. PATENT DOCUMENTS

| 9,266,233 B2 | 2/2016 | Kornbluh et al. |
| 9,498,401 B2 | 11/2016 | Herr et al. |

(Continued)

FOREIGN PATENT DOCUMENTS

| WO | 2016204441 A1 | 12/2016 |
| WO | 2019201982 A1 | 10/2019 |

OTHER PUBLICATIONS

ISR-WO for parent application PCT/EP2019/059900 (WO2019/201982) dated Aug. 26, 2019.

*Primary Examiner* — Timothy A Stanis
(74) *Attorney, Agent, or Firm* — Vorys, Sater, Seymour and Pease LLP

(57) ABSTRACT

A device and a method for actuating a joint of a human, an animal or a robot are disclosed. An elongated, lengthwise flexible and torsionally elastic body is provided for transmitting torque. Based at least in part on torsional deformation information of the body, torque is transmitted via the body. In an embodiment, a flexible drive shaft is provided, whereby the flexible drive shaft comprises said body. Furthermore, use of a flexible drive shaft as compliant element and as torque transmission element in a rotary actuator for actuating a mechanical joint is disclosed. In addition, use of a flexible drive shaft for determining an impedance of a joint of a human or an animal is also disclosed.

13 Claims, 14 Drawing Sheets

(51) Int. Cl.
  *B25J 9/16* (2006.01)
  *B25J 13/08* (2006.01)
(52) U.S. Cl.
  CPC .. *A61H 2201/149* (2013.01); *A61H 2201/165* (2013.01); *A61H 2201/1659* (2013.01); *A61H 2201/5061* (2013.01); *A61H 2201/5069* (2013.01); *A61H 2203/03* (2013.01)

(56) References Cited

U.S. PATENT DOCUMENTS

| | | |
|---|---|---|
| 2011/0040216 A1 | 2/2011 | Herr et al. |
| 2011/0066093 A1* | 3/2011 | Vess ............... A61H 11/00 601/151 |
| 2011/0313331 A1* | 12/2011 | Dehez ............ A61H 1/0285 601/33 |
| 2015/0096392 A1* | 4/2015 | Garrec ................ F16C 1/06 74/89.23 |
| 2017/0242477 A1 | 8/2017 | Rubin |
| 2018/0133894 A1 | 5/2018 | Choi et al. |
| 2018/0243881 A1* | 8/2018 | Campolo ............ B24B 49/16 |

\* cited by examiner

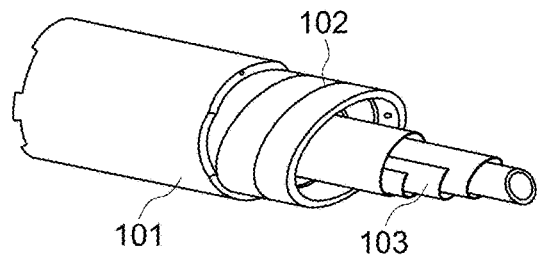 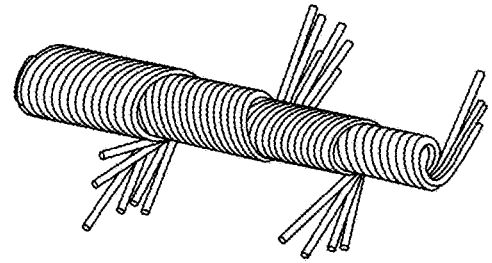
FIG. 1A  FIG. 1B
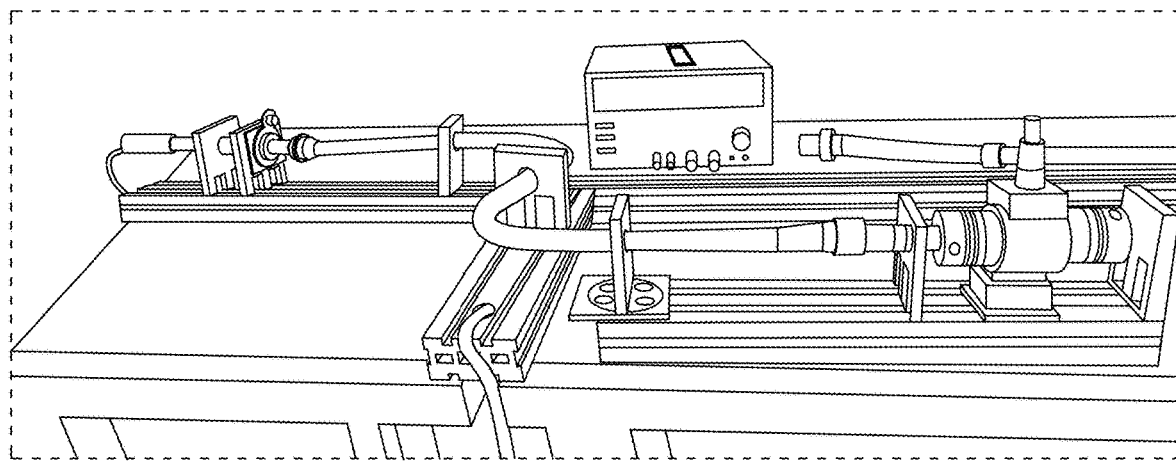
FIG. 2A
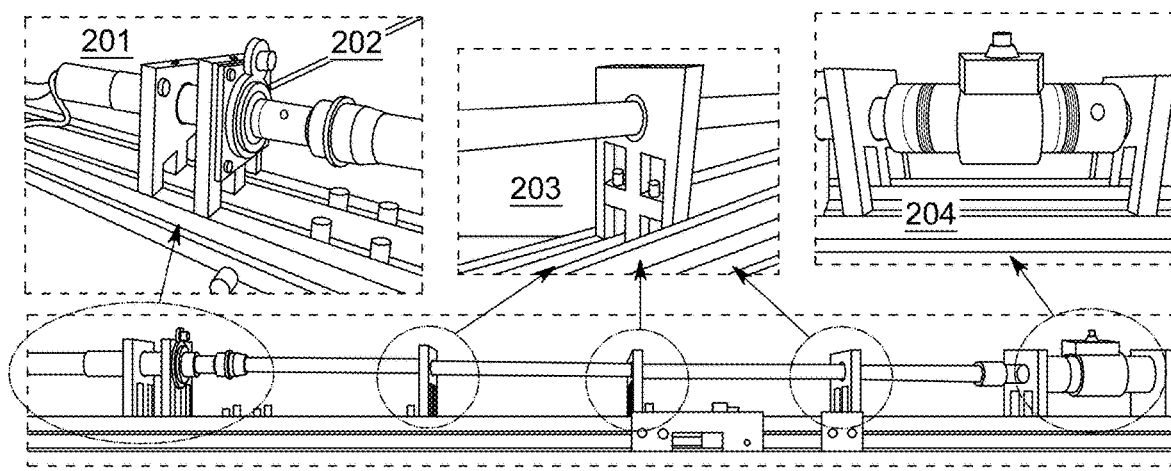
FIG. 2B

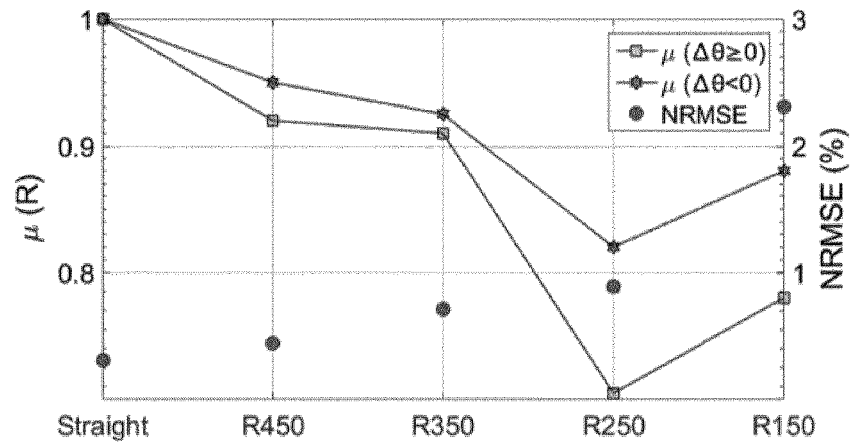
Fig. 9B
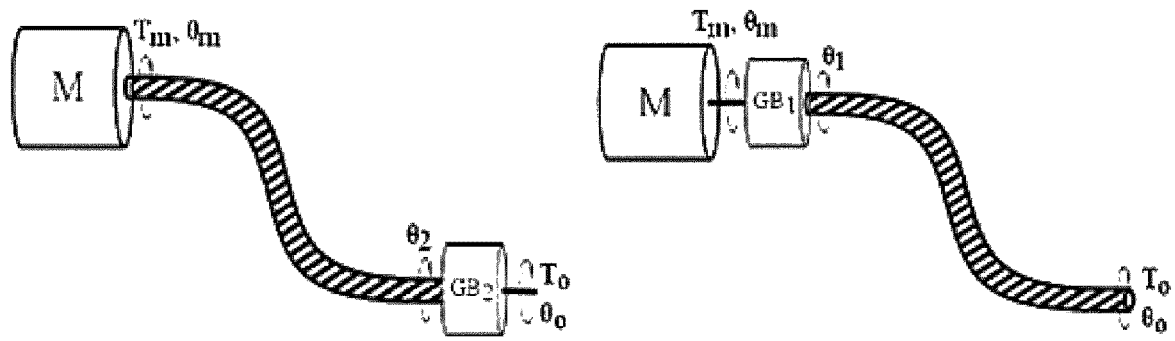
Fig. 10A  Fig. 10B
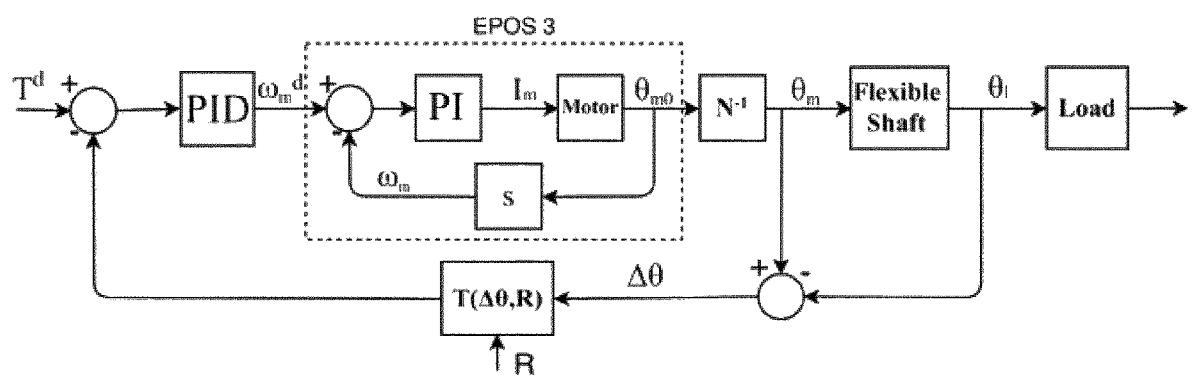
Fig. 11

DECENTRALIZED ROTARY ACTUATOR

TECHNICAL FIELD

The invention may in an aspect pertain to the technical field of prostheses not implantable in the body (IPC A61F 2/50) and in particular operating or control means therefor (IPC A61F 2/68). The invention may in an aspect pertain to deformation measurement and torsion control of a flexible drive shaft.

BACKGROUND

US 2011/0 040 216 A1, entitled "Exoskeletons for running and walking", describes a hip torque series elastic actuator. The series elastic actuator comprises a spring in series with an output of a motor/gearbox. The spring acts as a sensor, filter and impedance limiter.

The series elastic actuator requires the motor/gearbox to be close to and in-line with the joint rotational axis. At least one point of actuation is longitudinally displaced, making actuation inherently more intricate. For distal joints on limbs, such as knees, ankles, elbows and wrists, the presence of a motor near the joint imposes a large inertial load on the limb and requires additional power. In addition, for such joints, a motor/gearbox in line with the joint rotational axis may result in a bulky exoskeleton, i.e. a skeleton external to a human's or animal's body, thereby further impeding smooth movement.

D. Sahebjavaher, "Validation of the UBC Powered Upper Limb Orthosis Simulator", PhD Thesis, University of British Columbia (2012), http://dx.doi.org/10.14288/1.0103452, describes an exoskeleton comprising a flexible drive shaft to transmit motor power to a joint gearbox. Paragraph 2.3.2.1 of Sahebjavaher states that it is important to minimize the weight of the exoskeleton to minimize power requirements, inertial loads, and to keep the weight distribution of the device concentrated on the user's waist for ergonomic reasons, wherefore the flexible drive shaft is used.

Paragraph 3.2.1.3 of Sahebjavaher discusses that flexible drive shafts, due to their spring-damper like nature, introduce complications in predicting the actual performance of the drive system. Paragraph 3.2.1.3 furthermore notes that presence of bending in a flexible drive shaft produces unpredictable results. Paragraph 3.2.1.3 also discloses that if the flexible drive shaft is not guided, step responses significantly vary and are non-repeatable. To produce a consistent step response during orthosis operation, paragraph 3.2.1.3 proposes that the flexible drive shaft needs to be guided and that use of a tube casing is highly recommended to suppress non-axial rotational movements and vibrations throughout the length of the shaft.

M. R. Tucker et al., "Design of a wearable perturbator for human knee impedance estimation during gait", 2013 IEEE International Conference on Rehabilitation Robotics (ICORR) (2013), http://dx.doi.org/10.1109/ICORR.2013.6650372, discloses a knee perturbator to experimentally estimate human knee impedance during gait through the application of angular velocity perturbations. The knee perturbator comprises a portable lower-limb exoskeleton, designed specifically for switching between transparency and velocity control modes, and a bidirectional flexible drive shaft for remote actuation.

Tucker furthermore discloses in paragraph III.D that interaction torque between the perturbator and the shank of the leg is sensed using parallel dual grid strain gauges mounted to opposite sides of a crank arm of the exoskeleton. Tucker also proposes in paragraph IV an experimental characterization of the dynamic properties of the flexible shaft under different bending and loading conditions.

The teachings of Sahebjavaher and Tucker require a torque sensor at the joint to know the applied torque and to accurately drive the remote motor. A torque sensor is an expensive and delicate piece of equipment, which when placed at a joint may cause additional inertial load.

US 2018/0 133 894 A1 (also published under no. WO 2016/204 441 A1) discloses an articulated robot actuator. The actuator comprises two motors, a pair of joint actuating members, and a pair of spring members in between the motors and the joint actuating members for transmitting torque. The spring members may be torsionally deformed, i.e. may comprise torsion strain. A restoring force may be generated due to this torsional deformation. The pair of joint actuating members may include encoders on drive shafts thereof to measure rotation angles of the pair of joint actuating members and measure the degree of torsion strain of the pair of spring members on the basis of the rotation angles of the pair of joint actuating members. The articulated robot actuator may compensate for torque caused by the torsional deformation of the spring members by canceling the torsional deformation of the spring members by measuring a degree of torsional strain of the spring members and controlling the motors according to the degree of torsion strain. FIG. 5 of the document teaches that the encoders are all positioned at the distal end and off-axis from the spring members. The document further teaches that the motors, the spring members, and the pair of joint actuating members are positioned at the waist, whereby the pair of joint actuating members are coupled to the knee joint and/or hip joint via rigid link members.

US 2018/0 133 894 A1 remains silent on measuring longitudinal bending deformation of the spring members, i.e. a bending of the spring members around an axis perpendicular to the axis of torque transmission. As the joint actuating members are located at the waist, the spring members provide for compliance and local torque transmission, but not for remote torque transmission to the joint. This is provided via the rigid link members. Due to the local torque transmission, the embodiments of US 2018/0 133 894 A1 do not provide means for guiding the spring members, measuring spatial configuration of the spring members, and protecting the spring members.

The present invention aims to resolve at least some of the problems mentioned above.

SUMMARY OF THE INVENTION

In a first aspect, the present invention provides a device for actuating a joint of a human, an animal or a robot, according to claim 1.

In a second aspect, the present invention provides a method for actuating a joint of a human, an animal or a robot, according to claim 11.

In a third aspect, the present invention provides a use of a flexible drive shaft as compliant element and as torque transmission element in a rotary actuator for actuating a mechanical joint, according to claim 12.

In a fourth aspect, the present invention provides a use of a flexible drive shaft for determining an impedance of a joint of a human or an animal, according to claim 13.

The present invention is advantageous for several reasons. The elongated, lengthwise flexible and torsionally elastic body serves a dual purpose: decentralized torque transmission as well as compliant element in a rotary (torsional)

actuator, such as a rotary series elastic actuator. Decentralization (relocation) of the motor, e.g. to a stationary external position for a stationary exoskeleton or to the waist for a portable exoskeleton, keeps the inertial load in a distal limb joint or robotic arm limited, thereby limiting the power requirements and increasing user comfort and transparency. The body at least partially decouples the dynamics of the motor, including friction and inertia, and protects the motor against shocks introduced on the mechanical joint. The body can furthermore due to its torsional elasticity increase energy efficiency by storing and recoiling energy. The body also allows for relative movement of the motor and the mechanical joint.

Because of the compliance of the body, the device further needs an accurate drive system for generating a desired output torque. Torque sensors are delicate and expensive pieces of equipment, which should therefore be avoided. When placed at or near a distal limb joint, they also introduce inertial load, which is additionally disadvantageous. The present invention realizes accurate model-based torque control based on deformation information of the body, thereby mitigating the need for a torque sensor at or near the joint.

DESCRIPTION OF FIGURES

FIG. 1A shows a schematic representation of a flexible drive shaft. FIG. 1B shows a schematic representation of multiple concentric layers of windings comprising opposing pitch angles and directions.

FIGS. 2A and 2B show a dynamometric test benches.

FIG. 9B shows bending factors of a multiplicative torque model and the corresponding errors.

FIGS. 10A and 10B show schematic overviews of a system wherein a flexible drive shaft indirectly drives a joint via a transmission system (FIG. 10A) and a system wherein a flexible drive shaft directly drives a joint (FIG. 10B).

FIG. 11 shows a schematic representation of a cascade control system comprising an inner velocity control loop and an outer PID torque control loop.

DETAILED DESCRIPTION OF THE INVENTION

Figure 3:
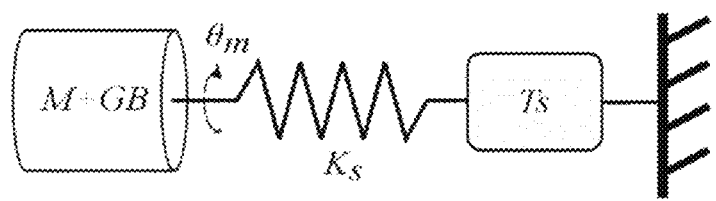
FIG. 3 shows a corresponding schematic overview thereof.

The present invention concerns a device and a method for actuating a joint of a human, an animal or a robot; use of a flexible drive shaft as compliant element and as torque transmission element in a rotary actuator for actuating a mechanical joint; use of a flexible drive shaft for determining an impedance of a joint of a human or an animal; and a system for determining an impedance of a joint of a human or an animal. The invention was summarized in the corresponding section above. In what follows, the invention is described in detail, preferred embodiments are discussed, and the invention is illustrated by means of examples.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

"Mechanical joint" as used herein refers to a non-human and non-animal joint comprising a first portion and a second portion which may relatively hinge.

The present invention involves an elongated, lengthwise flexible and torsionally elastic body. The "lengthwise flexibility" may lead to a "bending deformation" of the body. The "lengthwise flexibility" allows for varying "spatial configurations". The "torsional elasticity" may lead to a "torsional deformation" or "torsional strain" of the body. Each portion of the elongated body comprises a local length direction along which the body locally extends. One of ordinary skill in the art will appreciate that "torsional deformation" is associated with rotation around a rotational axis parallel to the local length direction and that "bending deformation" is associated with rotation around a rotational axis perpendicular to the local length direction. "Bending deformation" is hence associated with the spatial configuration of the body. The recitation of numerical ranges by endpoints includes all numbers and fractions subsumed within that range, as well as the recited endpoints.

The present invention provides a device for actuating a joint of a human, an animal or a robot. The device comprises a mechanical joint; a motor for providing torque to the mechanical joint; an elongated, lengthwise flexible and torsionally elastic body for transmitting torque from the motor to the mechanical joint; and a sensor cluster configured for determining torsional deformation information of the body. The device is in particular configured for driving the motor based at least in part on output from the sensor cluster.

The device is configured for driving the motor based at least in part on the torsional deformation information from the sensor cluster. Preferably, the device is configured for driving the motor without direct torque measurement at the body. Preferably, the device is configured for driving the motor without torque measurement at the mechanical joint. Preferably, the device is configured for driving the motor without torque measurement in between the body and the mechanical joint. Preferably, the device does not comprise a torque sensor in between the body and the mechanical joint. Preferably, the device does not comprise a torque sensor at the mechanical joint. Preferably, the device does not comprise a torque sensor at an end of the body.

In another aspect, the present invention provides a method for actuating a joint of a human, an animal or a robot. An elongated, lengthwise flexible and torsionally elastic body is provided. The body comprises a distal end and a proximal end. Torsional deformation information of the body is determined. An input, such as an input torque, an input velocity or an input position, for the proximal end of the body is determined based at least in part on a desired output torque at the distal end of the body and the torsional deformation information. The input is applied at the proximal end of the body. Hereby, input position is a synonym for input angle.

Preferably, the input is determined without torque measurement at the distal end of the body. Preferably, the input is determined without torque measurement at the mechanical joint. Preferably, the input is determined without torque measurement in between the body and the mechanical joint.

In a preferred embodiment, the device is configured for determining an input for the proximal end of the body based at least in part on a desired output torque at the distal end of the body and the output from the sensor cluster, whereby the device is further configured for applying said input at the proximal end of the body via the motor.

The present invention is advantageous for several reasons. The elongated, lengthwise flexible and torsionally elastic body serves a dual purpose: decentralized torque transmission as well as compliant element in a rotary (torsional) actuator, such as a rotary series elastic actuator. Decentralization (relocation) of the motor, e.g. to a stationary external position for a stationary exoskeleton or to the waist for a portable exoskeleton, keeps the inertial load in a distal limb joint or robotic arm limited, thereby limiting the power requirements and increasing user comfort and transparency. The elongated, lengthwise flexible and torsionally elastic body at least partially decouples the dynamics of the motor, including friction and inertia, and protects the motor against shocks introduced on the mechanical joint. The body can furthermore due to its torsional elasticity increase energy efficiency by storing and recoiling energy. The body also allows for relative movement of the motor and the mechanical joint.

Because of the compliance of the body, the device further needs an accurate drive system for generating a desired output torque. Torque sensors are delicate and expensive pieces of equipment, which should therefore be avoided. When placed at or near a distal limb joint, they also introduce inertial load, which is additionally disadvantageous. The present invention realizes accurate model-based torque control based on deformation information of the body, thereby mitigating the need for a torque sensor at or near the joint.

In yet another aspect, the invention provides a system for determining an impedance of a joint of a human or an animal. The system comprises a mechanical joint, which is externally applicable to the joint. The system further comprises an elongated, lengthwise flexible and torsionally elastic body. The body comprises a distal end and a proximal end. The body is directly or indirectly connectable at the distal end to the mechanical joint. A gearbox may, for example, be provided in between the distal end of the body and the mechanical joint. The system also comprises a sensor cluster configured for determining torsional deformation information of the body. In addition, the system comprises processing means configured for determining the impedance of the joint based at least in part on the torsional deformation information from the sensor cluster.

Preferably, the system does not comprise a torque sensor at the mechanical joint. Preferably, the system does not comprise a torque sensor at the distal end of the body. Preferably, the system does not comprise a torque sensor in between the body and the mechanical joint. Preferably, the processing means is configured for determining the impedance of the joint without torque measurement at the mechanical joint. Preferably, the processing means is configured for determining the impedance of the joint without torque measurement at the distal end of the body. Preferably, the processing means is configured for determining the impedance of the joint without torque measurement in between the body and the mechanical joint.

The system of the present invention hence realizes accurate impedance determination based on deformation information of the body, thereby mitigating the need for a torque sensor at or near the joint.

In a preferred embodiment, the device is configured for determining an impedance of the joint based at least in part on the output from the sensor cluster.

One of ordinary skill in the art will appreciate that a common technical feature is present in the various aspects of the present invention. One of ordinary skill in the art will furthermore appreciate that the different aspects of the present invention are interrelated. In the description above and in what follows, specific references to a particular aspect of the invention may be left out. All features described above or below may pertain to each of the different aspects, even if they have been described in conjunction with a particular aspect.

In a preferred embodiment, the torsional deformation information comprises a torsional relative angle between the distal end and the proximal end. Preferably, the sensor cluster is configured for determining a torsional relative angle between the distal end and the proximal end. Preferably, the output of the sensor cluster comprises one or more signals indicative of the torsional relative angle. Preferably, the sensor cluster comprises two rotational encoders, preferably rotational optical encoders. Preferably, at both of the distal and proximal ends of the body a rotational encoder is positioned in series. Based on data from the encoders, a torsional relative angle may be determined between the proximal and distal ends of the body. Said one or more signals may comprise absolute angle measurements. Additionally or alternatively, said one or more signals may comprise said torsional relative angle.

In a preferred embodiment, torsional deformation information as well as bending deformation information of the body are determined. Preferably, the bending deformation information comprises a bending angle or a bending radius. Preferably, the sensor cluster is configured for determining torsional deformation information and bending deformation information of the body. Preferably, the output of the sensor cluster comprises one or more signals indicative of the bending deformation information. Preferably, the device is configured for driving the motor based at least in part on the torsional and bending deformation information from the sensor cluster.

Preferably, an input for the proximal end of the body is determined based at least in part on a desired output torque at the distal end of the body and the torsional and bending deformation information. Preferably, the processing means are configured for determining the impedance of the joint based at least in part on the torsional and bending deformation information from the sensor cluster. Preferably, the sensor cluster comprises a distance sensor, a displacement sensor or an additional rotational encoder for determining the bending deformation information.

Bending of the body may influence the torque transmission characteristics of the body. It may therefore be important to take both torsional deformation information as well as bending deformation information into account for driving the motor to obtain a desired output torque at the distal end of the body. This way, an output torque at the distal end may obtained which lies closer to the desired output torque.

In a preferred embodiment, a torque model based on the torsional and bending deformation information is used. Preferably, the device is configured for driving the motor based at least in part on a torque model depending on the torsional and bending deformation information. Preferably, an input for the proximal end of the body is determined based at least in part on a desired output torque at the distal end of the body and a torque model based on the torsional and bending deformation information. Preferably, the processing means are configured for determining the impedance of the joint based at least in part on a torque model based on the torsional and bending deformation information. Preferably, the torsional deformation information is hereby the torsional relative angle. A torque model is often required for obtaining a sufficiently accurate modelling of the behavior of the body. The torque model may be a linear or a non-linear torque model, preferably a non-linear torque model.

Figure 22:
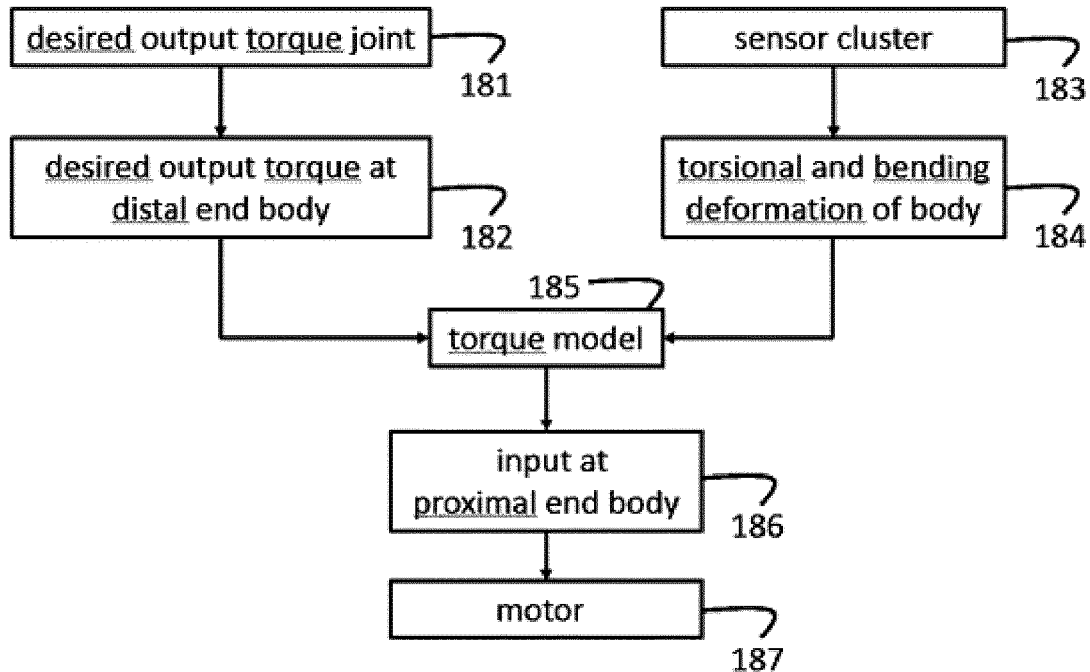
FIG. 22 shows a schematic overview of an embodiment of data flow for driving the motor.

FIG. 22 shows a schematic overview of an embodiment for driving the motor of the device. Preferably, the body is part of a flexible drive shaft. A desired output torque at the mechanical joint (181) is provided. The desired output torque at the joint may, for example, be based on a known gait cycle for the particular joint. The desired torque at the joint (181) may be converted to a desired output torque at the distal end of the body (182). Conversion may be required when, for example, a gearbox is positioned in series in between the distal end of the body and the mechanical joint. By means of a sensor cluster (183), torsional and bending deformation information of the body (184) is obtained. Hereby, the torsional deformation information is typically a torsional relative angle, as discussed above. Based on the desired output torque at the distal end of the body (182) and torsional and bending deformation information of the body (184), a torque model (185), preferably non-linear torque model, is utilized to calculate a corresponding input at the proximal end of the body (186). The input at the proximal end of the body (186) may be converted to information for driving the motor (187), for example a motor torque. Again, a gearbox may have been positioned in series in between the motor and the body, for example. Alternatively or additionally, the output of the torque model can be the driving information for the motor, such as a motor torque, a motor current, a motor position (motor angle) or a motor velocity. Conversion from input at the proximal end of the body (186) to information for driving the motor (187) is then implicitly incorporated in the torque model (185).

In a preferred embodiment, the dependency of the torque model, preferably non-linear torque model, on the torsional deformation information and on the bending deformation information is multiplicatively separable. The simulation of the body behavior is easier, quicker, and requires less computational resources when the torque model is multiplicatively separable. Moreover, a multiplicatively separable model is sufficiently accurate for the industrial applications of the present invention and shows that influence of bending and torsion on the behavior of the body can be calculated and understood separately.

The elongated and lengthwise flexible body is also torsionally elastic, i.e. the body comprises a limited torsional stiffness. The torque-angle relationship of the body may be non-linear. The torque-angle relationship of the body may be dependent on the rotational direction, i.e. clockwise or counterclockwise. In a preferred embodiment, the torsionally elastic body comprises a torsional stiffness of at most 10000 N·m/rad, preferably at most 7499 N·m/rad, more preferably at most 5623 N·m/rad, even more preferably at most 4217 N·m/rad, yet even more preferably at most 3126 N·m/rad, yet even more preferably at most 2371 N·m/rad, yet even more preferably at most 1778 N·m/rad, yet even more preferably at most 1334 N·m/rad, with greater preference at most 1000 N·m/rad, with even greater preference at most 750 N·m/rad, with a yet even greater preference at most 562 N·m/rad, and most preferably at most 422 N·m/rad. One of ordinary skill in the art will appreciate that a numerical value in the preceding list is an upper limit for the fraction of torque and angle along the torque-angle relationship of the torsionally elastic body. The torsionally elastic body may comprise a torsional stiffness, i.e. a fraction of torque and angle somewhere along the torque angle-relationship, of about 398 N·m/rad, about 316 N·m/rad, about 251 N·m/rad, about 200 N·m/rad, about 158 N·m/rad, about 126 N·m/rad, about 100 N·m/rad, about 79 N·m/rad, about 63 N·m/rad, about 50 N·m/rad, about 40 N·m/rad, about 32 N·m/rad, about 25 N·m/rad, about 20 N·m/rad, about 16 N·m/rad, about 13 N·m/rad, about 10 N·m/rad, about 7.9 N·m/rad, about 6.3 N·m/rad, about 5.0 N·m/rad, about 4.0 N·m/rad, about 3.2 N·m/rad, about 2.5 N·m/rad, about 2.0 N·m/rad, about 1.6 N·m/rad, about 1.3 N·m/rad, about 1.0 N·m/rad, about 0.79 N·m/rad, about 0.63 N·m/rad, about 0.50 N·m/rad, about 0.40 N·m/rad, about 0.32 N·m/rad, about 0.25 N·m/rad, about 0.20 N·m/rad, about 0.16 N·m/rad, about 0.13 N·m/rad, about 0.10 N·m/rad, about 0.079 N·m/rad, about 0.063 N·m/rad, about 0.050 N·m/rad, about 0.040 N·m/rad, about 0.032 N·m/rad, about 0.025 N·m/rad, about 0.020 N·m/rad, about 0.016 N·m/rad, about 0.013 N·m/rad, about 0.010 N·m/rad, or any value below or in between.

A flexible drive shaft may or may not have an outer casing. In a preferred embodiment, the body is the rotatable, elongated, lengthwise flexible and torsionally elastic inner shaft of a flexible drive shaft. Preferably, the device comprises a flexible drive shaft. Preferably, the method comprises the step of providing a flexible drive shaft. Preferably, the system comprises a flexible drive shaft. The flexible drive shaft comprises a rotatable, elongated, lengthwise flexible and torsionally elastic inner shaft, an outer casing, a distal end, a proximal end, and a connector on each of the distal and proximal ends. Hereby the body is the rotatable inner shaft. Preferably, the flexible drive shaft is a bidirectional flexible drive shaft. Preferably, the inner shaft comprises windings. Preferably, the inner shaft comprises several in essence concentric layers of windings. Preferably, the inner shaft comprises several consecutive in essence concentric layers of windings comprising opposing pitch angles and directions. Preferably, the windings comprise spring-grade wire.

A flexible drive shaft is advantageous for several reasons. The outer casing provides a bearing surface and support for the rotatable inner shaft. It also prevents excessive twisting of the inner shaft when submitted to high loads. A flexible drive shaft also has the further advantage that it comprises a higher efficiency than common other non-rectilinear torque transmission components, such as for example a universal joint.

FIG. 1A shows a schematic representation of an embodiment of a bidirectional flexible drive shaft. The flexible drive shaft comprises a rubber coating (101), an outer casing (102) and an inner core (103). FIG. 1B shows a schematic representation of the inner core (103) of the bidirectional flexible drive shaft. The inner core comprises multiple consecutive in essence concentric layers of windings comprising opposing pitch angles and directions. The windings comprise spring-grade wire.

The characteristics of a flexible shaft are determined at least in part by the grade of the wires, the size of the wires, the number of layers, the amount of wires in each layer, and the effective length of the flexible drive shaft. Typically, a trade-off between torsional stiffness and bending flexibility is made: if higher torsional stiffness is required, the bending flexibility and the minimum operating bend radius of the flexible drive shaft are reduced. This limits the spatial configuration of the flexible drive shaft. The length of the flexible drive shaft typically does not affect torque transmittance, but has an effect on torsional stiffness: the larger the length, the lower the torsional stiffness.

The torque-angle relationship of a bidirectional flexible drive shaft is typically non-linear and depends on rotational direction and bending deformation. When a torsional load is applied to the flexible drive shaft, half of its internal spring-like layers of wires try to expand as they unwind, while the alternate layers, above and below them, try to contract as they are wound tighter. This action, in which layers squeeze against each other under load, provides the torsional stiffness properties. However, when this torque is applied in a direction that causes the outer layer to expand, there is no other layer to resist it. This direction of operation, named the loosen-outer-layer (LOL) direction, will provide the lowest shaft stiffness. In contrast, the opposite direction, the tighten-outer-layer (TOL) direction, will provide the highest shaft stiffness.

Characterization of the torque transmission properties of a flexible drive shaft under dynamic loads and/or under deformation is important for accurately driving a mechanical joint or measuring an impedance via a mechanical joint.

A bidirectional flexible drive shaft comprises a non-symmetrical torque-angle relationship for clockwise and counterclockwise rotations. To obtain a more symmetrical torque-angle relationship, two flexible drive shafts may be connected in series, so that upon rotation always one of the flexible drive shafts is turning in its tighten-outer-layer (TOL) direction.

In another embodiment, the device and/or the system comprises two flexible drive shafts in parallel and configured to rotate in opposing directions upon transmitting torque. In this embodiment, both shafts are tightened together, but helix in opposite directions.

Figure 12A:
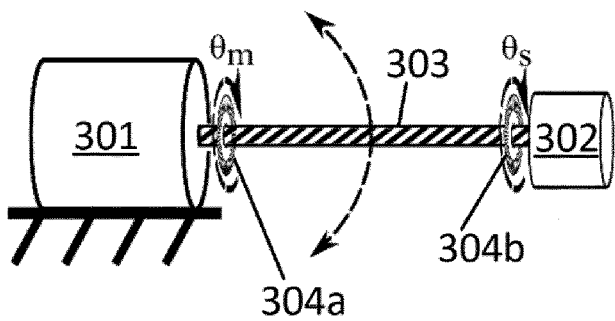
FIG. 12A shows a schematic overview of an embodiment of a device for actuating a joint of a human, an animal or a robot, comprising a mechanical joint (302), a motor (301) for providing torque to the mechanical joint, and an elongated, lengthwise flexible and torsionally elastic body (303), wherein the device is configured for transmitting torque from the motor (301) to the mechanical joint (302) via the body (303), wherein the device comprises a sensor cluster (304a, 304b) configured for determining torsional deformation information ($\theta_s$-$\theta_m$) of the body (303), and wherein the device is configured for driving the motor (301) based at least in part on output from the sensor cluster (304a, 304b).

The presence of a flexible drive shaft does not exclude presence of a rigid torque transmission shaft for portions where no bending is required. Therefore, the device may or may not comprise a rigid torque transmission shaft in series with the elongated, lengthwise flexible and torsionally elastic body, e.g. the flexible drive shaft. Likewise, the system may or may not comprise a rigid torque transmission shaft in series with the elongated, lengthwise flexible and torsionally elastic body, e.g. the flexible drive shaft. See FIG. 12A for an example.

In a preferred embodiment, a flexible drive shaft is used as compliant element and as torque transmission element in a rotary actuator for actuating a mechanical joint. Preferably, the flexible drive shaft is used to transmit torque from a motor to a target mechanical joint, wherein the motor and the target mechanical joint are mechanically coupled via one or more additional joints, wherein the flexible drive shaft is used to transmit torque over and/or through said one or more additional joints from the motor to said target mechanical joint. Preferably, the input from the motor for the flexible drive shaft is based at least in part on torsional and/or bending deformation information of the flexible drive shaft.

In a preferred embodiment, a flexible drive shaft is used for determining an impedance of a joint of a human or an animal. Preferably, the impedance is determined based at least in part on torsional and/or bending deformation information of the flexible shaft.

In a preferred embodiment, a transmission system, e.g. a gearbox or cable-pulley system, is provided in between the distal end of the body and the mechanical joint. Preferably, the device comprises a transmission system, e.g. a gearbox or cable-pulley system, in between the distal end of the body and the mechanical joint. Preferably, the system comprises a transmission system, e.g. a gearbox or cable-pulley system, in between the distal end of the body and the mechanical joint. Additionally or alternatively, a transmission system, e.g. a gearbox or cable-pulley system, may be provided at the proximal end of the body. In that case, the device may additionally or alternatively comprise a transmission system, e.g. a gearbox or cable-pulley system, in between the proximal end of the body and the motor. In that case, the system may additionally or alternatively comprise a transmission system, e.g. a gearbox or cable-pulley, at the proximal end of the body.

A gearbox in between the distal end of the body and the mechanical joint allows to enlarge the effective stiffness: when a gearbox is placed in series after the flexible shaft, the effective stiffness of the combination of the body and gearbox is the torsional stiffness of the body multiplied with the square of the reduction ratio of the gearbox.

In a preferred embodiment, the device for actuating a joint of a human, an animal or a robot is a wearable robot for actuating a joint of a human or an animal. Preferably, the wearable robot is an exoskeleton. The device may be a lower limb exoskeleton, an upper limb exoskeleton, a robotic arm, a prosthetics, or a haptic device.

The invention is further described by the following non-limiting examples which further illustrate the invention, and are not intended to, nor should they be interpreted to, limit the scope of the invention.

EXAMPLES

Example 1: Flexible Drive Shaft Characterization 1.1 Dynamometric Test Bench

FIGS. 2A and 2B show dynamometric test benches, comprising a motor (201), an encoder (202), a holder plate (203) and a torque sensor (204). FIG. 3 shows a corresponding schematic overview. M+GB denotes motor and gearbox able to provide a torque (angular rotation $\theta_m$) to a torsionally elastic (quasi-stiffness $K_s$) flexible drive shaft. A torque sensor measures the transmitted torque ($T_s$) at the distal end (output end) of the flexible drive shaft. The motor is a rotational EC motor (Maxon EC-4pole 30) by Maxon Motor Ag, equipped with an integrated 86:1 gearbox and a 500 counts per turn (CPT) Encoder. The motor can provide a continuous torque of 8 N·m, with intermittent torques up to 12 N·m and a continuous speed of 192 rpm. The motor is connected via a rod to the proximal end (input end) of the flexible shaft. A Maxon EPOS 3 controller can drive the motor at velocity control mode. The dynamometric test bench further comprises two rotational optical encoders (2000 CPT) placed at both ends of the flexible drive shaft. The difference of measured values between the two rotational optical encoders provides a measure of the relative torsional deflection angle of the flexible drive shaft. Data are sampled at 1 kHz by means of a Beckhoff EK 1000 module.

1.2 Flexible Drive Shafts Under Study

A first flexible drive shaft under study is the MasterFlex 08 comprising a diameter of about 8 mm, a length of about 86.5 cm, a maximum torque of about 6 N·m, and a total weight of about 1.2 kg. A second flexible drive shaft under study is the Dremel 225, comprising a diameter of about 3 mm, a length of about 20 cm, a maximum torque of about 0.22 N·m, and a total weight of about 0.3 kg. The first flexible drive shaft thereby comprises a higher torsional stiffness and lower bending flexibility than the second flexible drive shaft.

1.3 Straight Configuration

Initially, the first and second flexible drive shafts were placed horizontally and in essence without bending. The output end of the flexible drive shaft is connected to a torque sensor, which is blocked on its output and measures the torque that is being transmitted through the shaft. An encoder measures the position at the output of the motor unit ($\theta_m$), which provides information regarding the total deflection angle of the shaft. The motor is controlled in velocity mode and set to follow a torque multisine signal with a flat spectrum from 0.01 Hz to 10 Hz and variable amplitude within the maximum range of each flexible shaft.

Figure 4A:
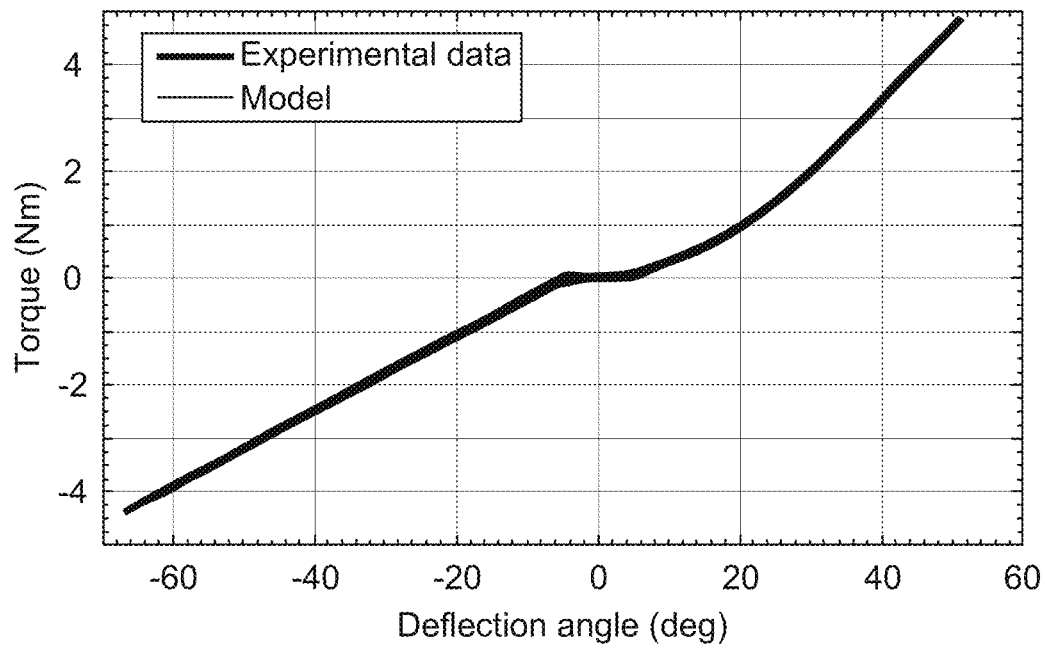
FIGS. 4A and 4B show the measured torque-deflection angle relationship of two flexible drive shafts in a straight configuration.
Figure 4B:
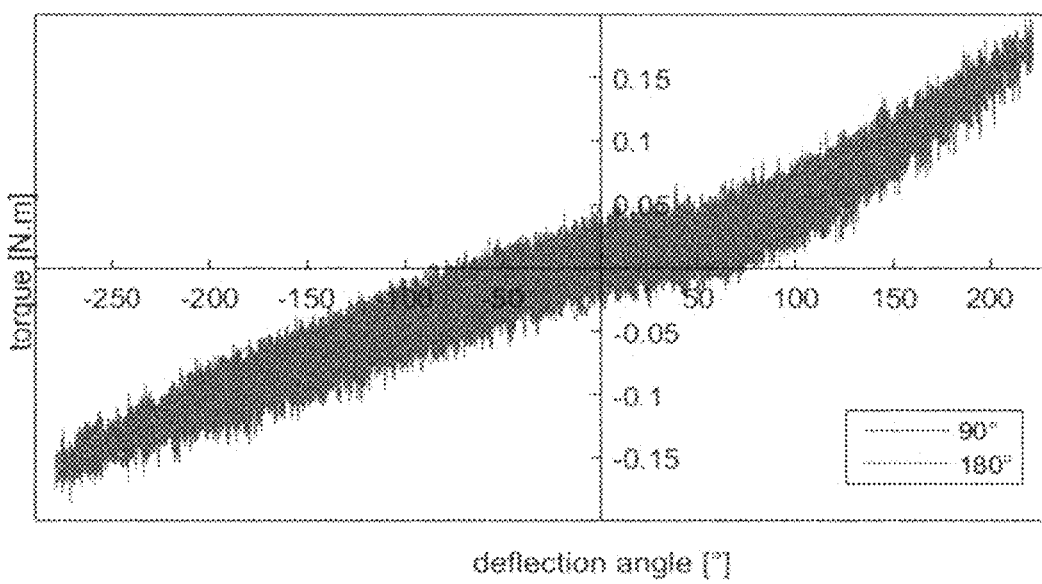

FIGS. 4A and 4B show the torque (Ts)-deflection angle ($\theta_m$) relationship of the first and the second flexible drive shaft, respectively. As can be observed, the relationship is non-symmetrical. The relationship comprises three different zones:

a quasi-linear zone, for negative deflection angles;
a deadzone, where no torque is exerted, for small values of deflection; and
a non-linear zone, for positive deflection angles.

1.4 Deformed Configuration

Figure 5A:
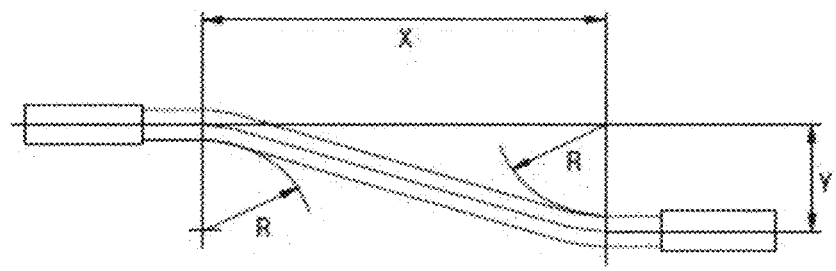
FIG. 5A shows a schematic overview of relative position parameters to compute a bend radius.
Figure 5B:
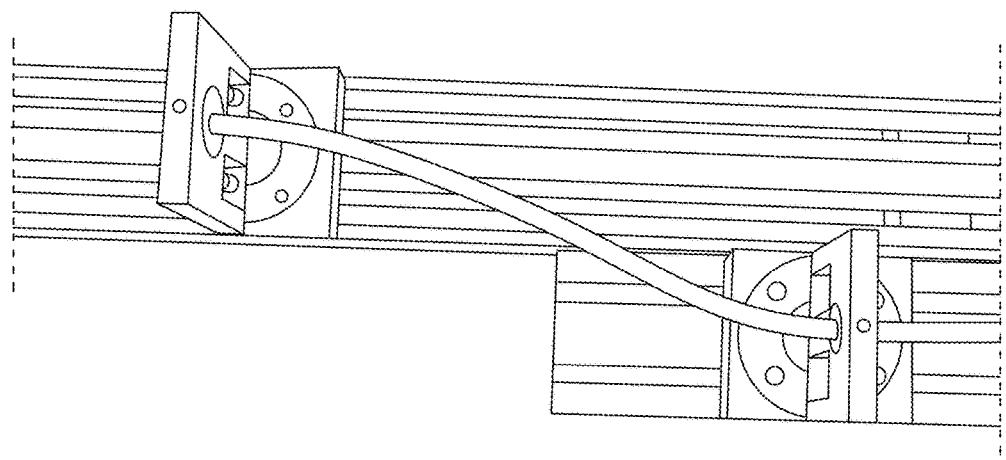
FIG. 5B shows a corresponding experimental setup.

The bending deformation may have influence on friction, torque capacity, and hence torque transmittance. Referring to FIG. 5A, a bent flexible drive shaft comprises incoming and outgoing portions in essence parallel to a common length direction and a bent portion in between. The bent portion comprises a displacement Y perpendicular to the length direction realized over a length X in the length direction. The bend radius R of a flexible drive shaft was computed as a function of the relative position of both sides of the flexible shaft (X, Y) via the formula $R=(X^2+Y^2)/(4Y)$. For this characterization, the motor and the torque sensor were placed on two different platforms that could move relative to each other in a two-dimensional Cartesian plane. In addition, holder plates were evenly distributed along the shaft to hold it in place and maintain a desired configuration during the experiments, see FIG. 5B. The motor was again operated as noted in preceding paragraph 1.3 of Example 1.

Figure 6:
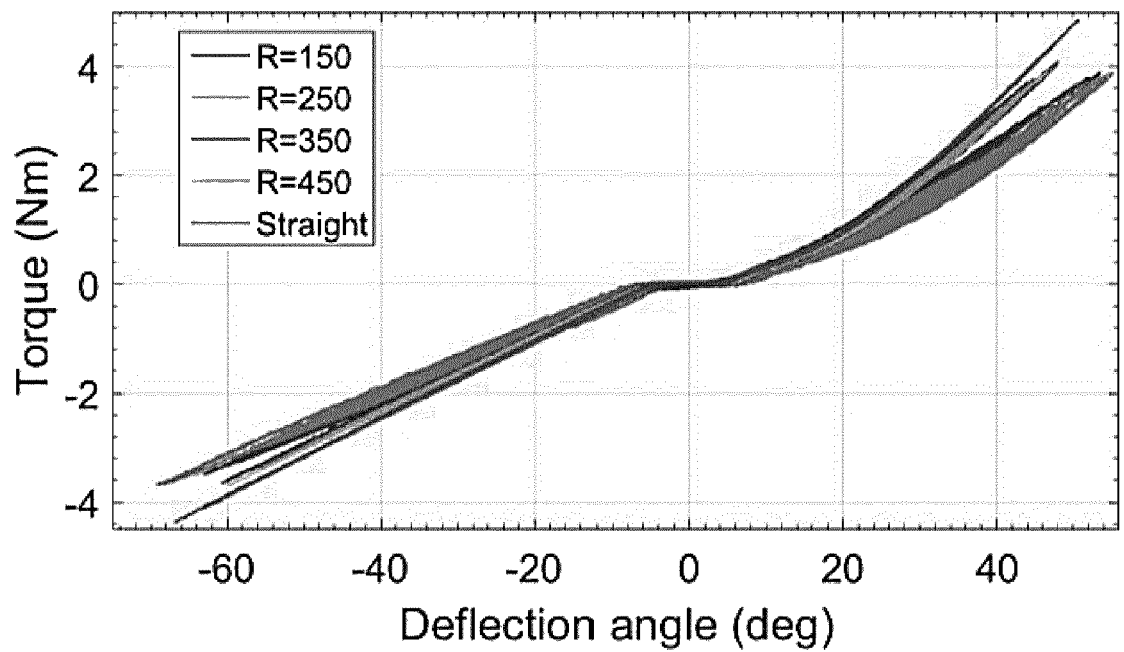
FIG. 6 shows the torque-angle relationship of a flexible drive shaft for different bend radii (in mm).

FIG. 6 shows the torque-deflection angle relationship for the first shaft under different bend radii R (in mm).

Figure 5C:
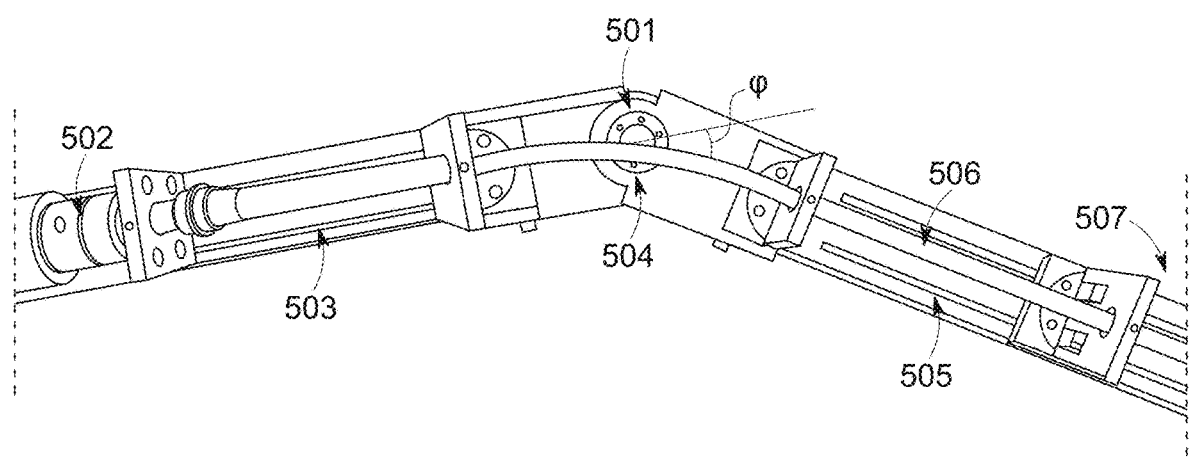
FIG. 5C shows an experimental setup for measuring a bend angle.

Alternatively or additionally to the bend radius R, the bending deformation information may comprise a bend angle φ, as indicated in FIG. 5C. The bend angle may be measured via a rotational encoder (504), such as a rotational optical encoder. The experimental setup further comprises a torque sensor (502), a drive unit (507), and a flexible shaft (506). The setup may model a knee joint (501) with a thigh (505) and a shank (503).

1.5 Output Torque-Angle Modelling for Straight Configuration

Flexible drive shafts are non-ideal torsion springs. The output torque vs. deflection angle relationship of flexible drive shafts depends on the torsional deflection angle and the bend angle. In addition, the relationship is non-symmetrical. Surprisingly, these relationships of flexible drive shafts show a high repeatability regardless of the amplitude or frequency of the setpoint command.

A two-component model is provided comprising a negative component for negative deflection angles and a positive component for positive deflection angles. With $\Delta\theta=\theta_m-\theta_s$, whereby $\theta_s=0$ for the performed tests, the torque $T_s$ and quasi-stiffness $K_s$ can be estimated for each of the positive and negative components with a Fourier series approximation and a dynamic-dependent term:

$$T_s(\Delta\theta) = \left[a_0 + \sum_{n=1}^{\infty}(a_n\cos(n\Delta\theta\omega) + b_n\sin(n\Delta\theta\omega))\right] + c\dot{\Delta\theta}$$

$$K_s(\Delta\theta) = \frac{dT_s(\Delta\theta)}{d\Delta\theta} = \left[\sum_{n=1}^{\infty}(nb_n\omega\cos(n\Delta\theta\omega) - na_n\omega\sin(n\Delta\theta\omega))\right] + c\ddot{\Delta\theta}$$

To account for the effect of the dynamics in the torque-angle curve, a dynamic-dependent term c, which considers the rotational velocity of the shaft was added.

TABLE 1

Fitted model coefficients for the first and second flexible drive shafts

| Coefficient | First flex. shaft (MasterFlex 08) | | Second flex. shaft (Dremel) | |
|---|---|---|---|---|
| | $\Delta\theta \geq 0$ | $\Delta\theta < 0$ | $\Delta\theta \geq 0$ | $\Delta\theta < 0$ |
| $a_0$ | 4.202 | −3.107 | 0.2207 | −0.08037 |
| $a_1$ | −4.201 | 2.335 | −0.2116 | 0.08088 |
| $a_2$ | — | 0.7484 | −0.007712 | 0.0003384 |
| $a_3$ | — | 0.02559 | — | — |
| $b_1$ | 0.1622 | −1.487 | −0.03922 | −0.0063 |
| $b_2$ | — | 0.3618 | 0.0213 | 0.01242 |
| $b_3$ | — | 0.1976 | — | — |
| c | 0.00003 | 0.00003 | 0.0005 | 0.0005 |
| ω | 0.03322 | 0.04357 | 0.007123 | 0.01114 |

Figure 7A:
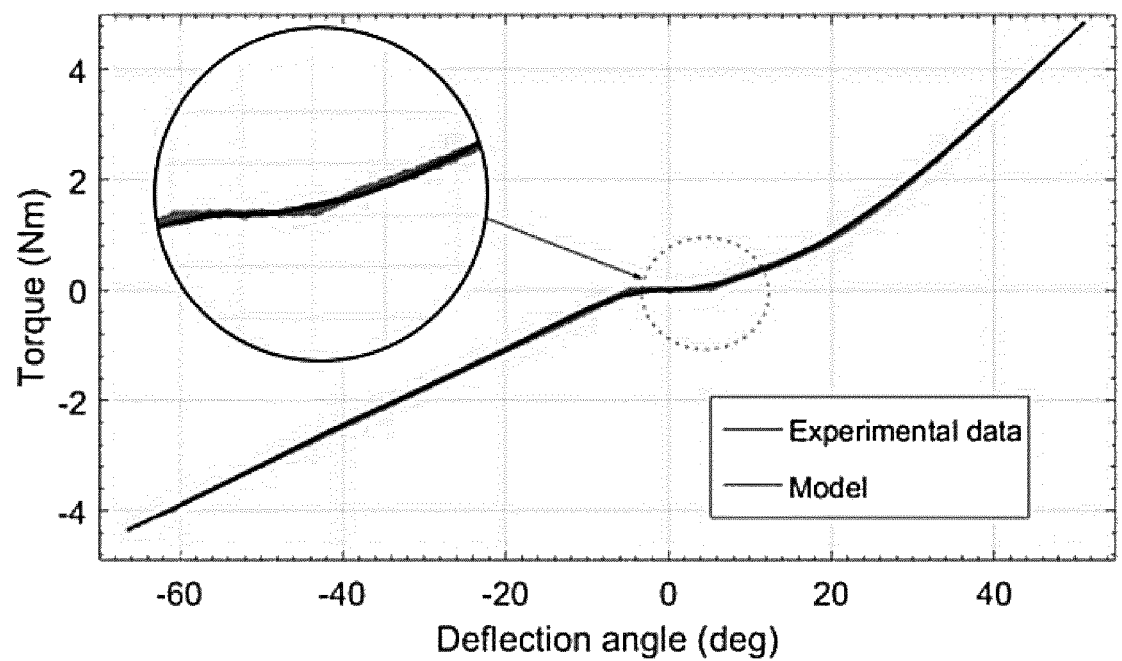
FIGS. 7A and 7B show correspondence of the measured and predicted torque-deflection angle relationships in the straight configuration.
Figure 7B:
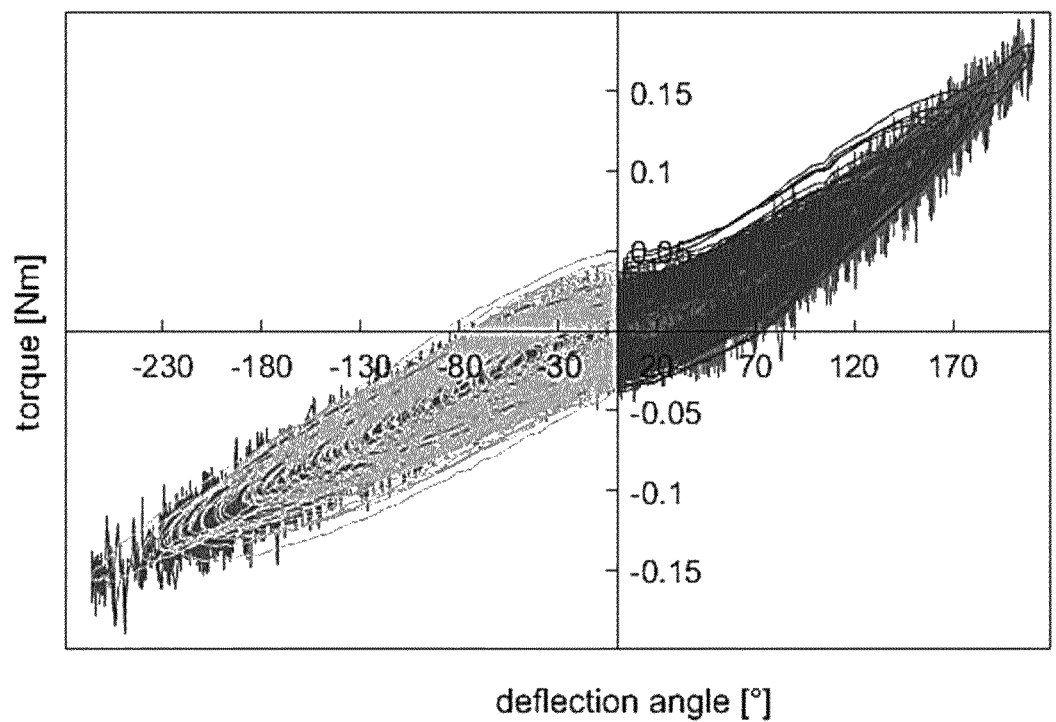
Figure 8A:
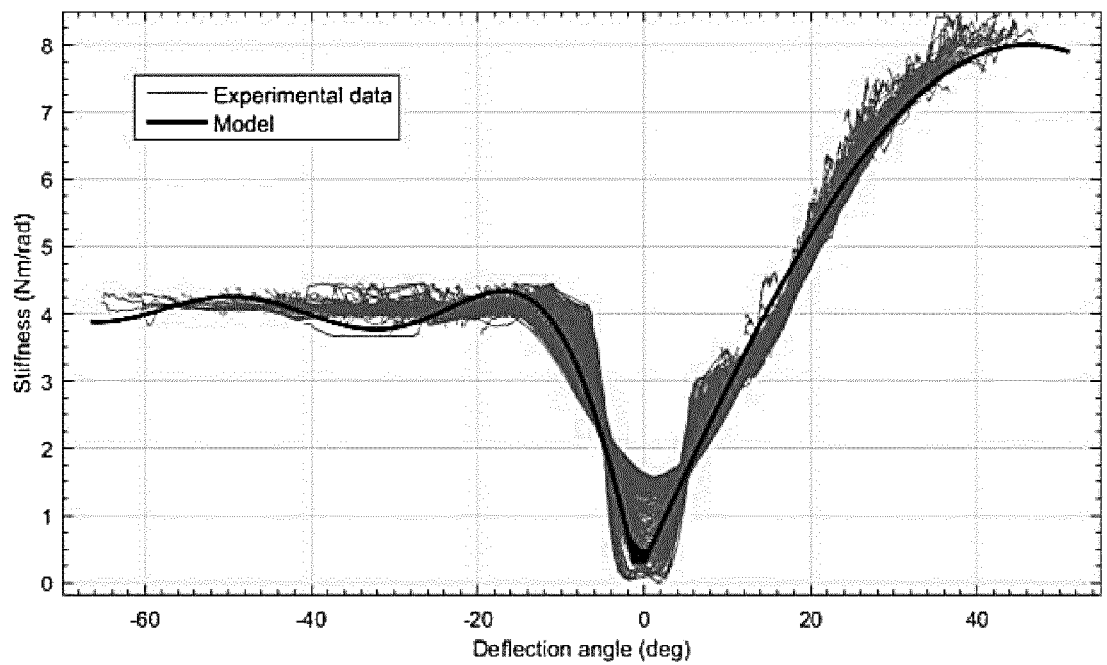
FIGS. 8A and 8B show correspondence of the measured and predicted quasi-stiffness—deflection angle relationships in the straight configuration.
Figure 8B:
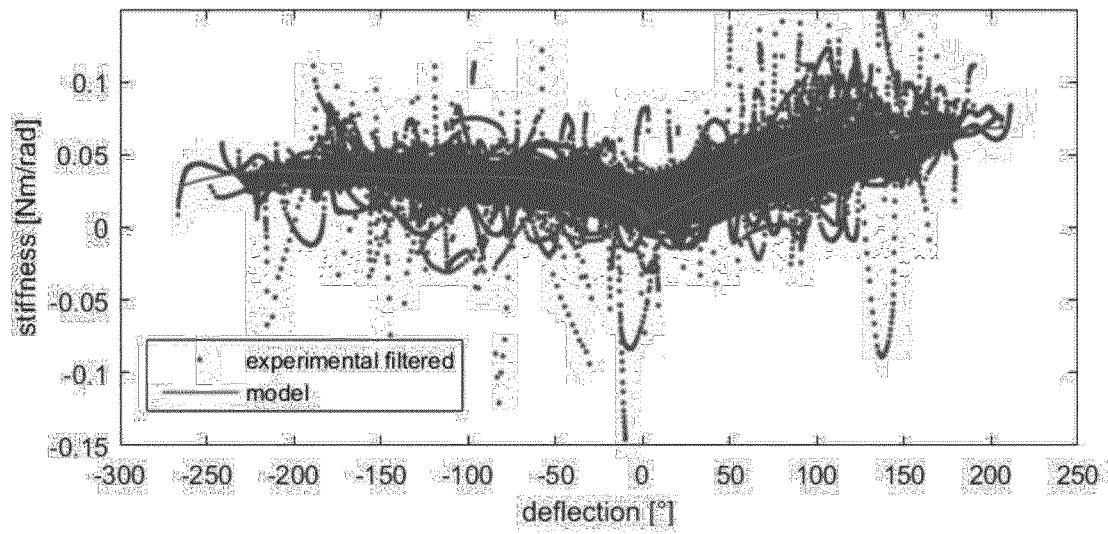

Table 1 comprises fitted model coefficients for the first and second flexible drive shafts. The corresponding experimental and model torque-angle relationships of the first and second flexible drive shafts are shown in FIGS. 7A (first flex. shaft) and 7B (second flex. shaft). The model shows a root mean square error of 0.029±0.017 N·m with respect to the torque values provided by the torque sensor. The normalized root mean square error is 0.315±0.188%, with maximum observed values of 1.27%. The corresponding experimental and model quasi-stiffness-angle relationships of the first and second flexible drive shafts are shown in FIGS. 8A (first flex. shaft) and 8B (second flex. shaft).

1.6 Output Torque-Angle Modelling for Bending Deformation

It was surprisingly found that a model multiplicatively separable in its dependence on bending deformation R and relative torsional angle $\Delta\theta$, i.e. $T_s(\Delta\theta, R)=\mu(R)\cdot T_s(\Delta\theta)$ and $K_s(\Delta\theta, R)=\mu(R)\cdot K_s(\Delta\theta)$, provides surprisingly accurate results.

Figure 9A:
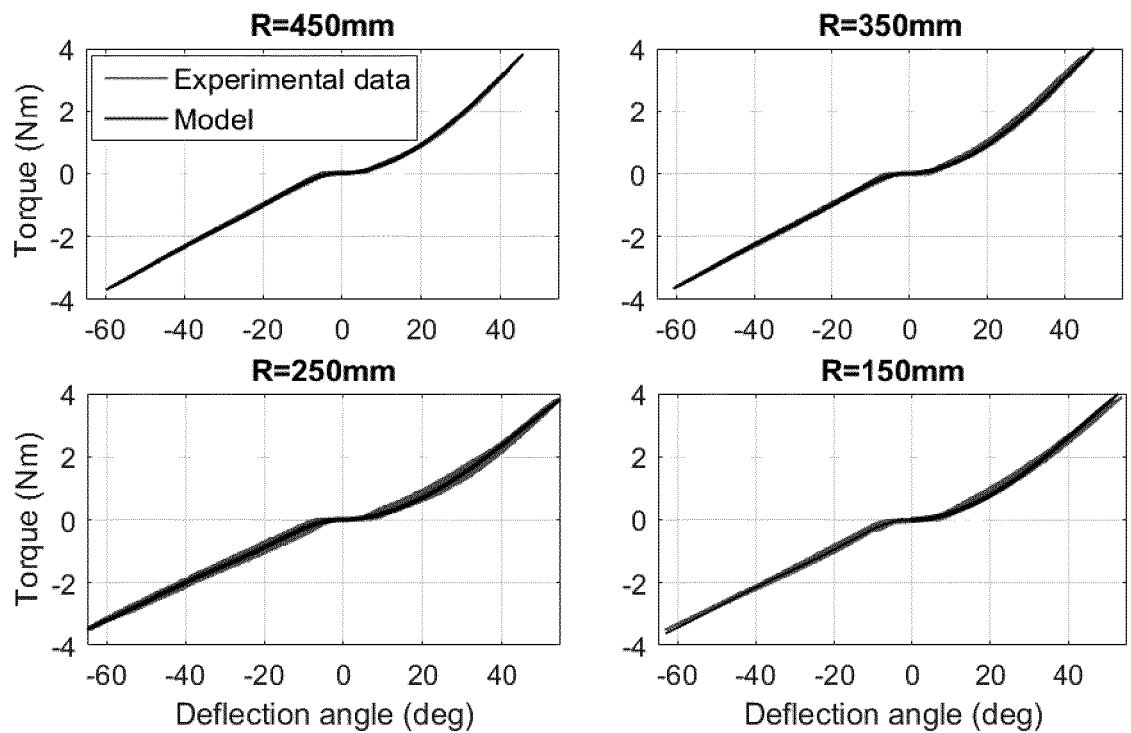
FIG. 9A shows correspondence of the measured and predicted torque-deflection angle relationships for several bend radii.

Table 2 and FIG. 9B comprise fitted bending deformation prefactors $\mu(R)$ at various bend radii R for the first flexible drive shaft, as well as the corresponding normalized root mean square errors between the experimental data and the model predictions. The corresponding experimental and model torque-angle relationships of the first flexible drive shaft are shown in FIG. 9A for various values of the bend radius R.

TABLE 2

Fitted bending deformation prefactor $\mu(R)$

| | First flex. shaft (MasterFlex 08) | | |
|---|---|---|---|
| R (mm) | $\mu$ ($\Delta\theta \geq 0$) | $\mu$ ($\Delta\theta < 0$) | NRMSE |
| 150 | 0.78 | 0.88 | 2.31% |
| 250 | 0.705 | 0.82 | 0.89% |
| 350 | 0.91 | 0.925 | 0.71% |
| 450 | 0.92 | 0.95 | 0.44% |
| Straight | 1 | 1 | 0.31% |

A simple methodology to model torque transmittance (or quasi-stiffness) properties of two different flexible drive shafts has been obtained, considering both their dynamics and spatial configuration. This allows for accurate estimation of torque transmission through the flexible drive shaft based only on the torsional deflection and bend radius, without the need for a torque sensor.

Example 2: Flexible Drive Shaft Directly Driving an Output Joint

In case of wearable robots, the most important parameters are torque, velocity and stiffness achieved at the output of the actuator. With a flexible drive shaft directly driving an output joint or in series with a 1:1 transmission system, cfr. FIG. 10B, a highly compliant actuator, such as a series elastic actuator (SEA), is obtained which allows for accurate torque control at the output joint level with intrinsic safety properties. Advantages include torque control at the output based on position sensors (angle measurement), safety in case of shocks introduced by the load, and energy storing capabilities.

FIG. 11 shows a cascade control system comprising an inner velocity control loop performed at the motor controller (EPOS3) and an outer PID torque control loop. Output torque is calculated using the separable model $T_s(\Delta\theta, R)=\mu(R)\cdot T_s(\Delta\theta)$.

Figure 14:
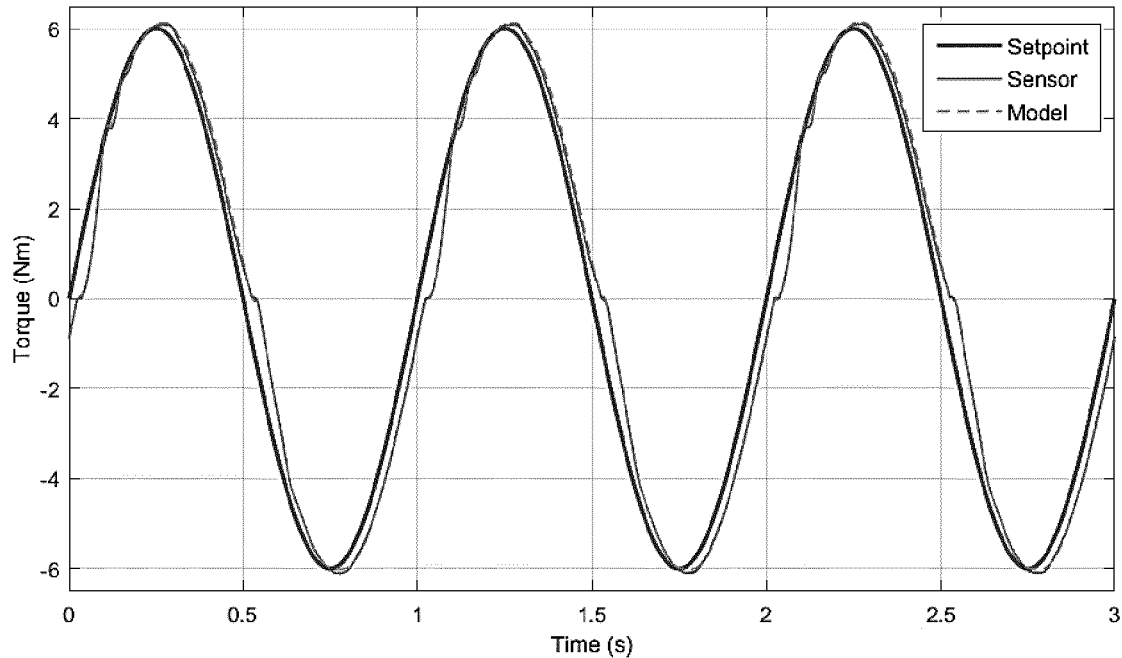
FIG. 14 shows the performance of the control system in following a setpoint signal with the configuration represented in FIG. 10B.

FIG. 14 shows the performance of the implemented controller when following a desired sinusoidal signal with an amplitude of 6 N·m and a frequency of 1 Hz. The tracking error shows a mean value (RMSE) of 0.7334±0.0223 N·m for a set of 15 iterations, corresponding to a normalized error (NRMSE) of 6.11%, with a mean delay of 25 ms. However, the mean error in accuracy between the torque estimation and the torque sensor is 0.0456±0.005 N·m (0.37%).

Figure 15:
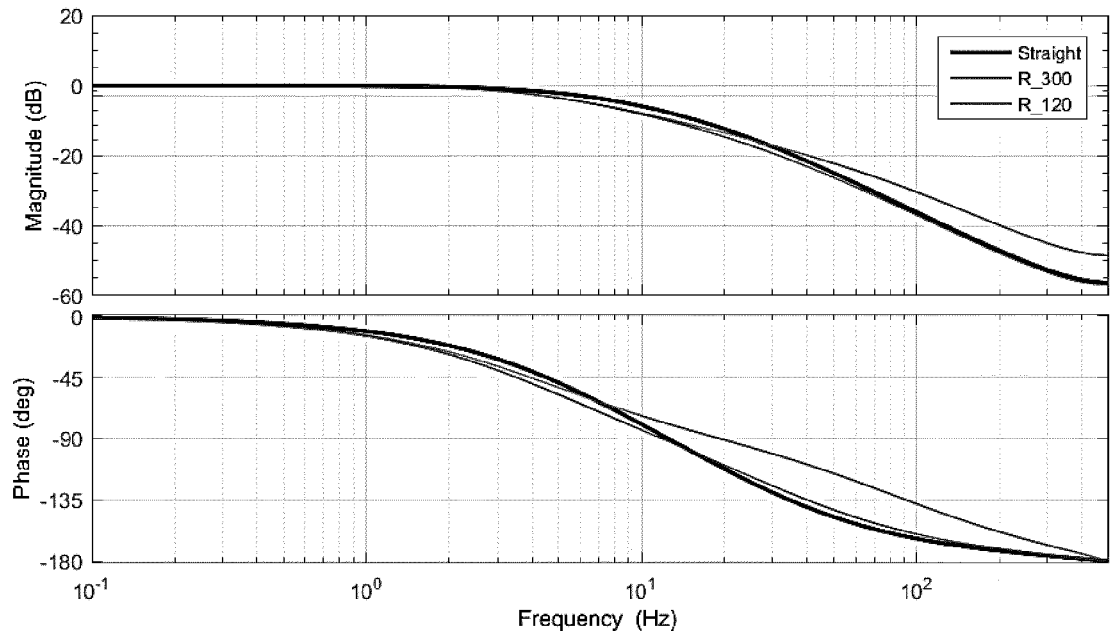
FIG. 15 shows a corresponding bodeplot for various bend radii.

The bandwidth of the same controller has been assessed as well. A multisine signal with a flat spectrum from 0.1 Hz to 10 Hz and variable amplitude with a peak value of 5 N·m was used as setpoint of the torque controller for the bend radii 450, 300 and 120 mm, as well as for straight conditions. FIG. 15 shows a bodeplot of the approximated second order transfer functions $G(s)=T_{estimated}/T_{desired}$ for three of the four conditions that were tested. These transfer functions were estimated using MATLAB's system identification toolbox and fitted the measured data with an accuracy close to 80% for all the tested conditions. The controller shows a bandwidth, calculated as the cutoff frequency at an attenuation of −3 dB, of 6.22 Hz when the cable is straight. As the cable is set in configurations with lower bend radius (higher bending), the bandwidth decreases to 5.87 Hz, 4.32 Hz and 4.30 Hz for bend radii of 450, 300 and 120 mm, respectively.

Example 3: Impedance of a Flexible Drive Shaft at Zero Torque Control

In order to perform good torque control in robots interacting with humans, an accurate actuation system with low impedance is desired. The active orthosis must follow the joint motion, so that the subject does not feel any resistance, when the desired torque is set to zero. In order to check the output impedance of the flexible drive shaft under zero torque control (transparent mode), a motor was connected at its output in order to act as an external disturbance. The motor was set in position control mode, to follow a chirp signal with a frequency swept of 0.1 to 10 Hz and an amplitude of 20 degrees. The torque controller was set to 0 N·m, so that the input motor would react to the output disturbance in a way that this load does not feel any restriction. Again, the torque estimation was used as feedback for the torque control, giving a measure of the interaction torque between the load and the actuator. A torque sensor was placed in between the load motor and the flexible drive shaft in order to compare the interaction torque values with the estimations.

Figure 16:
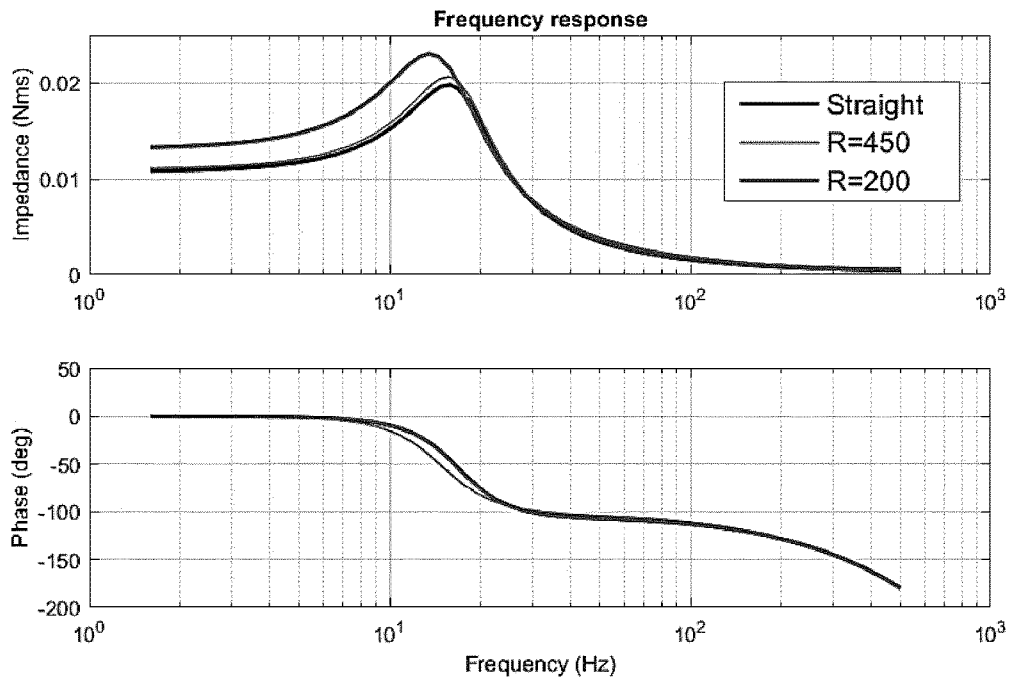
FIG. 16 shows the measured impedance of a flexible drive shaft at various bend radii.

Output impedance was calculated as the transfer function between the interaction torque (provided by the estimation) and the output velocity generated by the load motor, for three different conditions: straight shaft and bend radii of 450 and 200 mm. This way, the influence of bend radius on the output impedance was characterized. As FIG. 16 shows, the controller is able to render impedances close to zero for low frequencies regardless of the bend radius. As the frequency is increased, the controller cannot fully follow the desired output impedance and starts to display higher ones, until the resonance point is reached and the output impedance becomes the mechanical impedance of the flexible shaft. This output impedance increases more for lower bend radius. In addition, the maximum impedance value (resonance point) is achieved at lower frequencies as the cable is bent. The output impedance of the flexible drive shaft depends not only on the controller, but also on the spatial configuration of the flexible drive shaft, due to the increase in friction with bend radius. The flexible drive shaft therefore behaves as a variable stiffness actuator, as its output stiffness depends on the spatial configuration of the flexible shaft.

Figure 13:
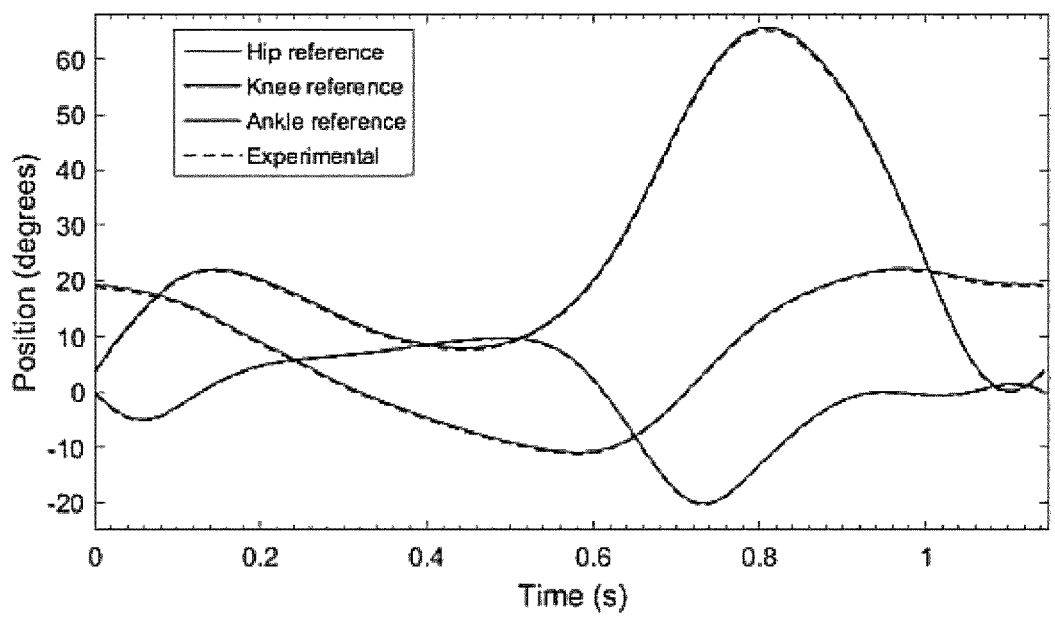
FIG. 13 shows human-like position profiles for a hip, knee and ankle joint.
Figure 17:
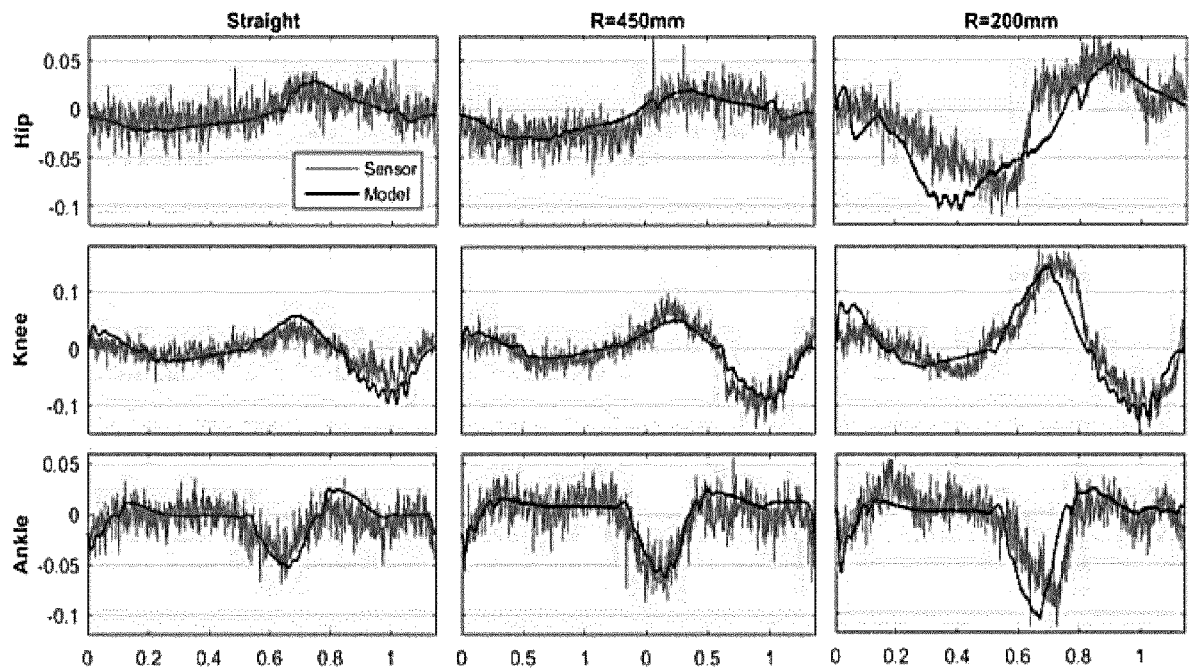
FIG. 17 shows interaction torque time profiles for imposed human-like external disturbance trajectories of human hip, knee and ankle joint.

In order to test the interaction torque a human would feel when using the proposed actuator and controller, the load motor was set to follow a human-like position profile for the hip, knee and ankle joint as shown in FIG. 13, taken from human data (D. A. Winter, Biomechanics and Motor Control of Human Movement, 2009) at a speed of 1.2 s/stride, which is considered a normal walking speed. Results on interaction torques are given in FIG. 17, where the measurement from the torque sensor is compared to the one provided by the model estimation. The model accurately predicts the interaction torque. The proportional part of the PID control can therefore be increased, improving the response of the system.

Example 4: Flexible Drive Shaft with Transmission System at an Output Joint

In case of wearable robots, the most important parameters are torque, velocity and stiffness achieved at the output of the actuator. By directly driving an output joint with a flexible drive shaft, cfr. FIG. 10B, the output torque is limited by the maximum capacity of the flexible drive shaft. The torque that can be transmitted by a flexible drive shaft is limited and depends mainly on the diameter. Therefore, if higher torques are required thicker flexible drive shafts are needed, which increases its size and weight and limits the maximum bending. Another option is to increase the output torque by means of a transmission system at the output end, cfr. FIG. 10A, with a reduction ratio higher than 1. This way, thinner and lighter flexible drive shafts can be implemented. In exchange, output velocity is reduced and output stiffness enlarged, limiting the compliant properties of the actuator and reducing the accuracy of the torque controller due to possible backlash or losses in the transmission system. In particular, the output stiffness is increased by the square of the transmission ratio, increasing the output impedance of the device, losing the compliant properties of the actuator, and turning it into a stiff actuator.

In a corresponding test, a gearbox with transmission ratio 9:1 was placed at the distal end of the flexible drive shaft. The gearbox was connected to a torque sensor in order to measure the generated output torque. The transmission sensor can be taken into account multiplicatively in the torque model, and again good correspondence of measured and predicted torques was obtained.

Example 5: Dynamic Bending

In this example, the bend angle $\varphi$ instead of the bend radius R is used to characterize the bending deformation, see FIG. 5C. The motor (507) and the torque sensor (502) are placed in two different aluminum profiles that act as the thigh (505) and the shank (503), respectively, connected by a passive hinge joint which acts as the knee joint (501). The flexible drive shaft (506) connects the motor with the torque sensor (502), transmitting the torque from the thigh to the ankle, spanning through the knee joint. A rotational optical encoder (504) measures the rotation angle $\varphi$ of the knee, providing information of the flexible shaft's bend angle. The shaft is rigidly and evenly fixed to the two profiles by means of custom made holding plates.

The torque controller was set to follow a 1 Hz sinusoidal signal with an amplitude of 4 N·m while the joint's angle was manually changed to fixed angles of 0, 20, 40, 60, 70, 80 and 90 degrees while the output torque was measured by the torque sensor. Data were collected and implemented in an offline identification procedure to update the model estimation to consider the bend angle by means of the deformation prefactor $\mu(\varphi)$. The identified deformation prefactors ($\mu(\varphi)$-values) were introduced into a dynamic lookup table, with linear interpolation for $\mu(\varphi)$. This way, the torque estimation was automatically set to be updated as a function of the bend angle, measured by the knee encoder.

Figure 18:
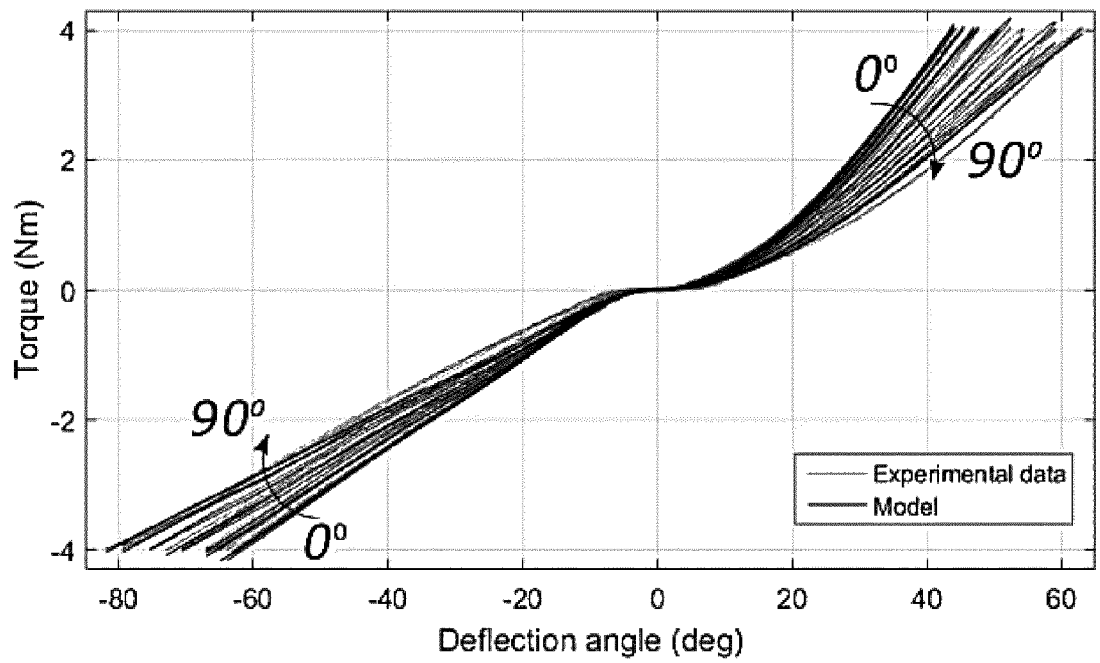
FIG. 18 shows the effect of the bend angle in a flexible drive shaft's output torque-angle characteristic.

FIG. 18 shows the effect of the bend angle in the shaft's output torque-angle characteristic, as well as the ability of the proposed model to dynamically track these changes by means of the separable model $T_s(\Delta\theta, \varphi)=\mu(\varphi)\cdot T_s(\Delta\theta)$ using a lookup table with linear interpolation to update $\mu(\varphi)$ as a function of the bend angle $\varphi$ for the sinusoidal signal of 4 N·m and 1 Hz.

Figure 19:
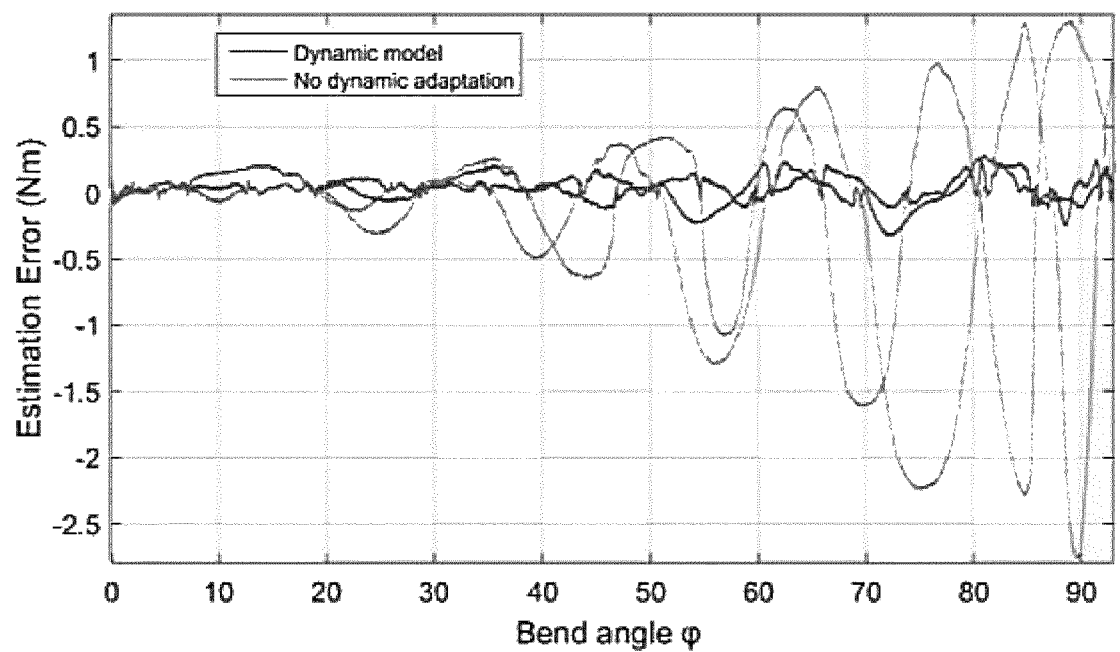
FIGS. 19 and 20 show estimation error profiles.
Figure 20:
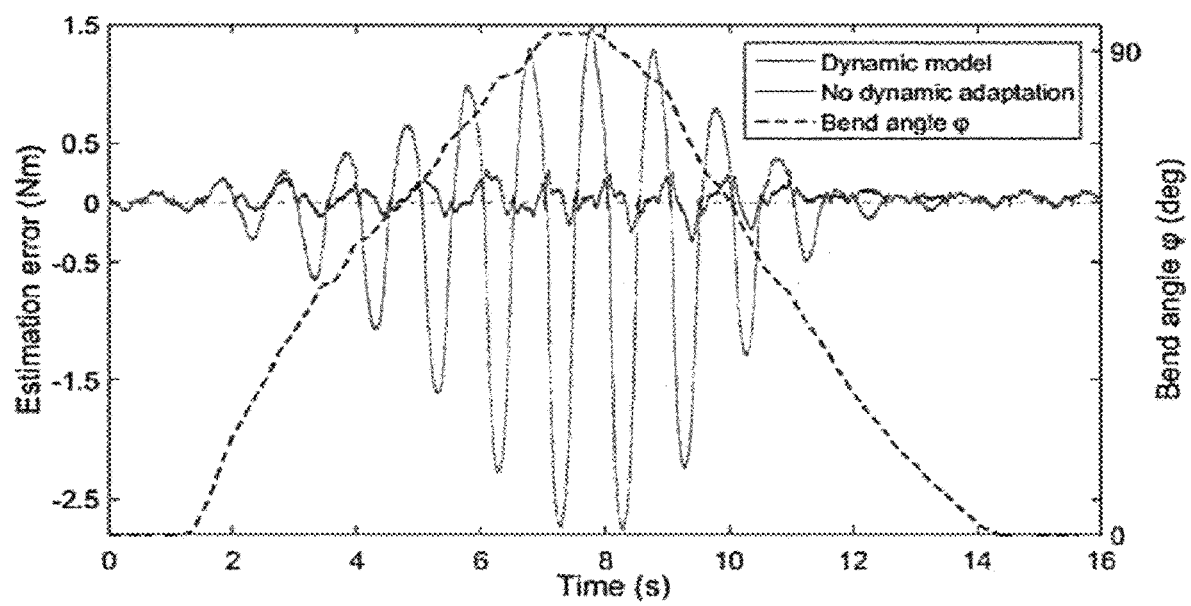

FIG. 19 shows the estimation error as a function of the bend angle, and FIG. 20 a corresponding time evolution of the estimation error and the bend angle, both using the proposed dynamic model and without it. Maximum estimation error when using the dynamic adaptation was 0.35 N·m, whereas the maximum estimation error in case of neglecting the effect of the bend angle was 2.8 N·m. The proposed adaptive model reduces the accuracy error by 87.5% by considering the bend angle.

Example 6: Sensor Cluster for Deformation Information of the Body

This example describes a preferred embodiment of the sensor cluster of the device, the method, and the system. Hereby, the body is preferably part of a flexible drive shaft.

The sensor cluster comprises two rotational encoders for determining the torsional deformation information. The rotational encoders are preferably rotational optical encoders, preferably with 2000 counts per turn (CPT). 2000 CPT corresponds to a precision of 0.18°. One of the rotational encoders is positioned in series at the proximal end of the body and another of the rotational encoders is positioned in series at the distal end of the body. Based on the signals from the two rotational encoders, the torsional relative angle between the distal end and the proximal end can be determined.

The sensor cluster comprises one or more bending sensors for determining bending deformation information of the body. A bending sensor may hereby be a distance sensors, a displacement sensors, an additional rotational encoder, and the like. A bending sensor may directly measure a deformation of the body or may measure a deformation of another component, e.g. the mechanical joint, to which the body is attached. If the body comprises several flexion points along its length (and correspondingly the wearable robot, orthosis or exoskeleton), each of these flexion points may be provided with the necessary bending sensors.

Example 7: An Embodiment of the Device

Figure 21:
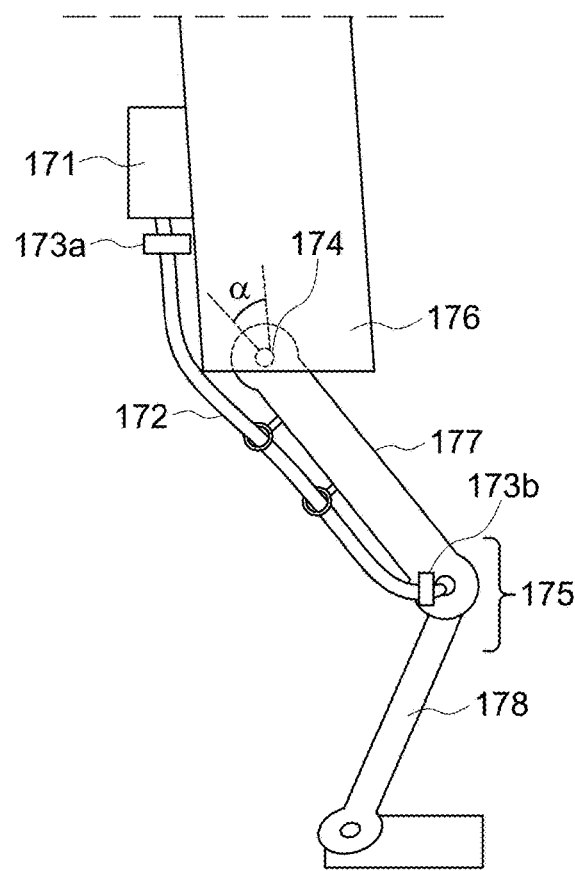
FIG. 21 shows a schematic overview of an embodiment of a device for actuating a joint.

FIG. 21 shows a schematic overview of an embodiment of the device for actuating a joint. The device comprises a mechanical joint (175), a motor (171) for providing torque to the mechanical joint (175), a flexible drive shaft (172) in between the motor (171) and the mechanical joint (175) for transmitting torque from the motor (171) to the mechanical joint (175).

The device further comprises a sensor cluster (173a, 173b, 174). The sensor cluster comprises:
- a first rotational optical encoder (173a) positioned in series in between the motor (171) and the proximal end of the flexible drive shaft (172);
- a second rotational optical encoder (173b) positioned in series in between the distal end of the flexible drive shaft (172) and the mechanical joint; and
- a bending sensor (174).

Based on output from the first and second rotational encoders (173a, 173b), a relative torsional angle of the flexible drive shaft can be obtained. Based on the bending sensor (174) bending deformation information of the flexible drive shaft can be obtained, such as, for example, a bending angle ($\alpha$) or a bending radius.

The motor may hereby be positioned on the back of a torso (176), while the mechanical joint may be a knee mechanical joint (175) for rotating a lower leg (178) relative to an upper leg (177).

The motor is driven based on a non-linear torque model (185; see FIG. 18) to calculate an input, preferably an input velocity, such as a motor velocity, at the proximal end of the flexible drive shaft (186) based on a desired output torque at the distal end of the flexible drive shaft (182) and the torsional relative angle and bending deformation information of the flexible drive shaft (184). The schematic overview of FIG. 18 is discussed in detail in the preceding description above. Due to the torque model no torque sensor is required at the mechanical joint, at the distal end of the flexible drive shaft or in between the mechanical joint and the distal end of the flexible drive shaft.

Decentralization of the motor and driving the motor based on a torque model provide the advantages as discussed in the preceding description above.

Example 8: Comparison with Traditional In-Line Torque Provision

A remote and torsionally compliant actuator (RTCA) comprising a Maxon EC-4pole 30 motor, a MasterFlex 08 flexible drive shaft, two rotational encoders, and a gearbox has a total weight of 1.8 kg, where 0.7 kg corresponds to the input motor plus gearbox combination, and can deliver a maximum torque of 4 to 6 N·m with a torque bandwidth which ranges from 4.3 to 6.22 Hz depending on the flexible shaft's spatial configuration. Although the weight of the RTCA is comparable to other compliant actuators with similar torque ranges, the RTCA improves the mass distribution on the exoskeleton as its weight is uniformly distributed over the limb, instead of being concentrated at the joint level. Besides, using the presented output torque estimation model, the flexible shaft is turned into a virtual torque sensor for the RTCA that only uses position encoders to estimate and control the output torque delivered at the joint level without the need for a real torque sensor, which is generally expensive, bulky and heavy and is normally placed at the joint location, having also a negative impact on the inertia of the system.

Figure 12B:
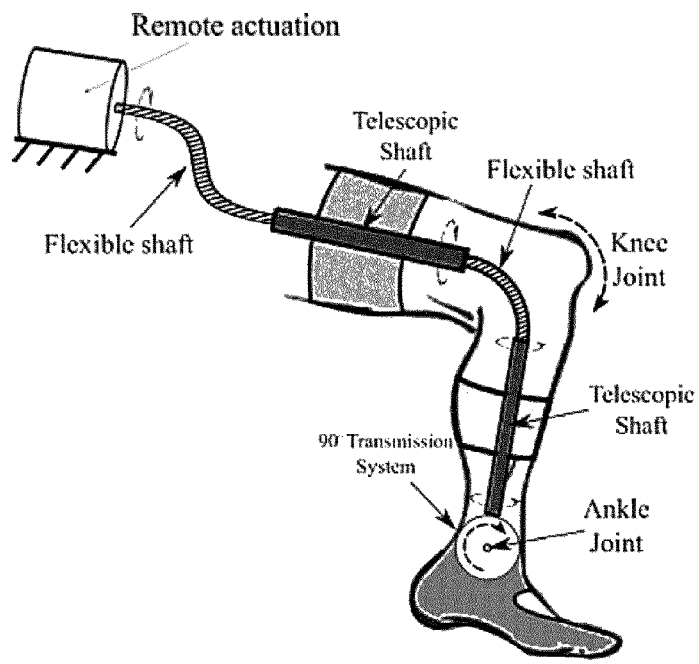
FIG. 12B shows a schematic overview of an embodiment of a device for actuating an ankle joint.

In order to study the effect of the remote actuation approach on the torque requirements, a lower limb exoskeleton was simulated using SimMechanics (MATLAB, The MathWorks, Inc), in which only the ankle joint is actuated. Human-like position trajectories were imposed at the hip and knee joints (see FIG. 13), and the required torque to drive the joints was compared using inverse dynamics, both when implementing the RTCA to drive the ankle joint (see FIG. 12B), and when using a traditional approach where the actuator is directly placed in-line with the ankle. The exoskeleton size was adapted for a 1.70 m height human using anthropometric data, giving a length of 0.416 m for the thigh and 0.418 m for the shank. Weight was distributed within the exoskeleton as follows:
- For the RTCA, the motor weight (0.7 kg) was modelled as a punctual mass located at 0.1 m from the hip joint and connected to the thigh. The weight of the flexible shaft together with the rest of the components were modelled as a mass of 1.1 kg located at 0.1 m from the knee joint.
- As for the in-line approach, a total weight of 1 kg was estimated for an actuator implementing the same input motor-gearbox combination as the RTCA, with a weight of 0.7 kg, and 0.3 kg extra that includes a compliant element (typically a torsion spring) and the required auxiliary components.

Figure 23A:
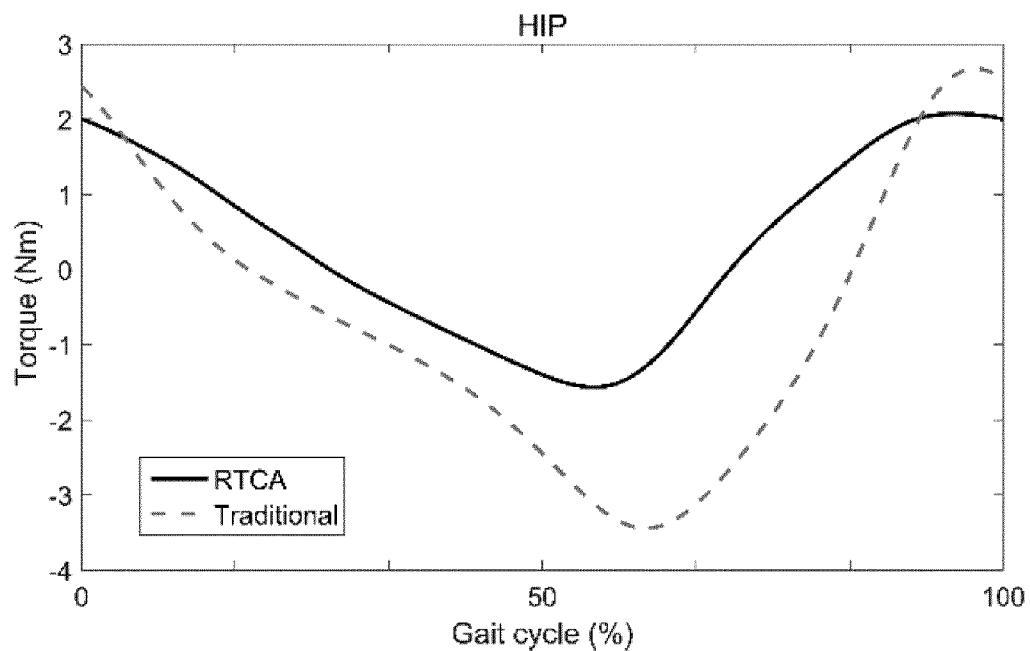
FIGS. 23A and 23B show required torques at hip and knee joints, respectively, to accelerate and deaccelerate an ankle joint actuator during a gait cycle, using a remote and torsionally compliant actuator (RTCA) according to an embodiment of the present invention (full line), and according to a traditional in-line approach (dashed line).
Figure 23B:
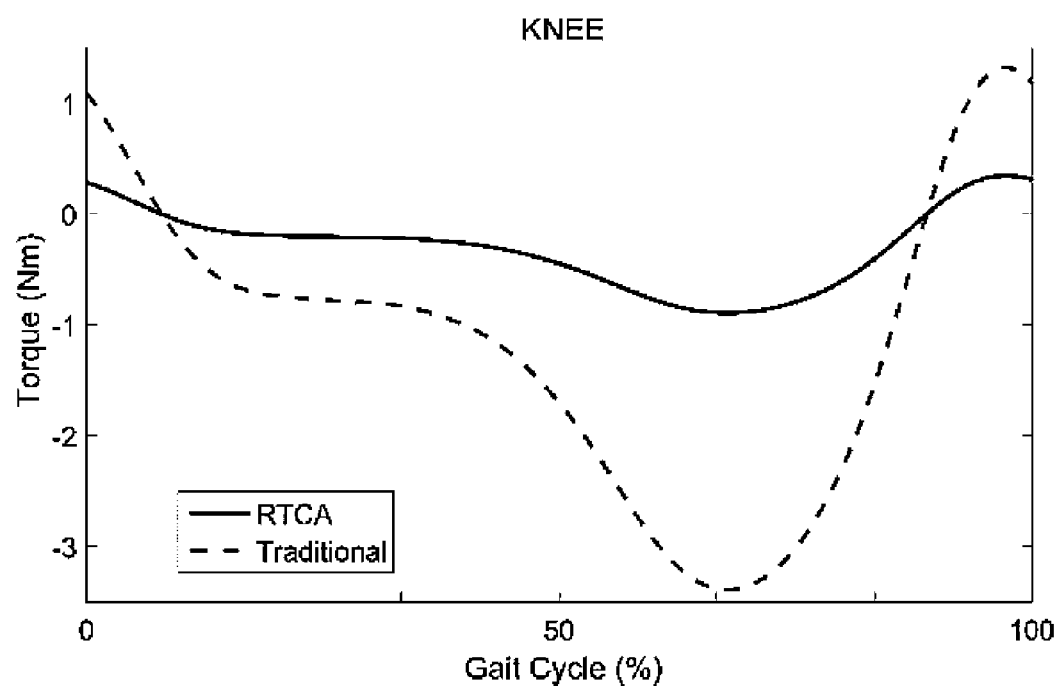

FIGS. 23A and 23B show the results from the simulations. FIGS. 23A and 23B show required torques at hip and knee joints, respectively, to accelerate and deaccelerate an ankle joint actuator during a gait cycle, using a remote and torsionally compliant actuator (RTCA) according to an embodiment of the present invention (full line), and according to a traditional in-line approach (dashed line).

For the hip joint, the peak torques required to accelerate and deaccelerate the ankle actuator when imposing human-like kinematic profiles at the hip and knee joint are reduced from 2.67 Nm in extension and 3.45 Nm in flexion, when using a traditional actuator placed at the ankle, to 2.07 Nm in extension and 1.56 Nm in flexion when using the proposed RTCA approach. This means a peak decrease of 22.5% of the required extension torque and of 54.8% for the flexion torque at the hip joint. For the knee joint, the required peak extension torques are reduced from 3.39 Nm to 0.89 Nm (73.75% decrease) and from 1.32 Nm to 0.35 Nm for flexion torques (73.5%).

Finally, simulation results showed the use of a RTCA can highly reduce the amount of torque required to accelerate the self-weight of an exoskeleton due to the better weight distribution. For the case of the ankle joint, results showed a decrease of 55% of the peak required torque at the hip and of 74% at the knee when compared to an in-line traditional actuation approach.

The invention claimed is:

1. Device for actuating a joint of a human, an animal or a robot, comprising:
 a mechanical joint;
 a motor for providing torque to the mechanical joint; and
 an elongated, lengthwise flexible and torsionally elastic body, whereby the device is configured for transmitting torque from the motor to the mechanical joint via the body, wherein the device further comprises a sensor cluster configured for determining torsional deformation information of the body, whereby the device is configured for driving the motor based at least in part on output from said sensor cluster,
  wherein the device comprises a flexible drive shaft, the flexible drive shaft comprising a rotatable, elongated, lengthwise flexible and torsionally elastic inner shaft, an outer casing, a distal end, a proximal end, and a connector on each of the distal and proximal ends, whereby said body is said rotatable inner shaft.

2. Device according to claim 1, wherein the body comprises a distal end and a proximal end, wherein the sensor cluster is configured for determining a torsional relative angle between the distal end and the proximal end, and wherein said output comprises one or more signals indicative of said torsional relative angle.

3. Device according to claim 2,
 wherein the device is configured for driving the motor based at least in part on a torque model depending on said torsional relative angle and said bending deformation information, and
 wherein the sensor cluster is configured for determining bending deformation information of the body, and wherein said output comprises one or more signals indicative of said bending deformation information.

4. Device according to claim 2,
 wherein the device is configured for driving the motor based at least in part on a torque model depending on said torsional relative angle and said bending deformation information, and
 wherein said bending deformation information comprises a bending angle or a bending radius.

5. Device according to claim 1, wherein the sensor cluster is configured for determining bending deformation information of the body, and wherein said output comprises one or more signals indicative of said bending deformation information.

6. Device according to claim 5, wherein said bending deformation information comprises a bending angle or a bending radius.

7. Device according to claim 5, wherein the device is configured for driving the motor based at least in part on a torque model depending on said torsional relative angle and said bending deformation information.

8. Device according to claim 7, wherein the dependency of said torque model on said torsional relative angle and said bending deformation information is multiplicatively separable.

9. Device according to claim 1, wherein the body comprises a distal end and a proximal end, wherein the device is configured for determining an input for the proximal end of the body based at least in part on a desired output torque at the distal end of the body and said output from said sensor cluster, and wherein the device is further configured for applying said input at the proximal end of the body via said motor.

10. Device according to claim 1, wherein the device is configured for determining an impedance of the joint based at least in part on said output from said sensor cluster.

11. Device according to claim 1, wherein the torsionally elastic body comprises a torsional stiffness of at most 10000 N·m/rad.

12. Device according to claim 1, wherein said device is a wearable robot for actuating a joint of a human or an animal.

13. Method for actuating a joint of a human, an animal or a robot, comprising the steps of:
 providing an elongated, lengthwise flexible and torsionally elastic body comprising a distal end and a proximal end;
 determining torsional deformation information of the body; and
 determining an input for the proximal end of the body based at least in part on a desired output torque at the distal end of the body and the torsional deformation information; and
 applying the input at the proximal end of the body,
  the method further comprises the step of providing a flexible drive shaft, the flexible drive shaft comprising a rotatable, elongated, lengthwise flexible and torsionally elastic inner shaft, an outer casing, a distal end, a proximal end, and a connector on each of the distal and proximal ends, whereby said body is said rotatable inner shaft.

* * * * *